US012602193B1

(12) United States Patent
Kurfirst et al.

(10) Patent No.: US 12,602,193 B1
(45) Date of Patent: Apr. 14, 2026

(54) METHODS AND SYSTEMS FOR VIRTUAL ASSISTANCE USING A DEVICE

(71) Applicant: CVS Pharmacy, Inc., Woonsocket, RI (US)

(72) Inventors: Dwayne Kurfirst, Woonsocket, RI (US); Neema Athia, Woonsocket, RI (US); Dhiren R. Solanki, Woonsocket, RI (US)

(73) Assignee: CVS Pharmacy, Inc., Woonsocket, RI (US)

( * ) Notice: Subject to any disclaimer, the term of this patent is extended or adjusted under 35 U.S.C. 154(b) by 0 days.

(21) Appl. No.: 18/916,021

(22) Filed: Oct. 15, 2024

(51) Int. Cl.
| | |
|---|---|
| *G06F 3/14* | (2006.01) |
| *A61B 5/00* | (2006.01) |
| *A61B 5/024* | (2006.01) |
| *G02B 27/01* | (2006.01) |
| *G06F 3/01* | (2006.01) |

(Continued)

(52) U.S. Cl.
CPC .............. *G06F 3/14* (2013.01); *A61B 5/0022* (2013.01); *A61B 5/02416* (2013.01); *A61B 5/6893* (2013.01); *G06F 3/017* (2013.01); *G06F 40/20* (2020.01); *G06F 40/40* (2020.01); *G06T 7/0012* (2013.01); *G06V 10/774* (2022.01); *G06V 20/597* (2022.01); *G06V 40/28* (2022.01); *G02B 27/0101* (2013.01); *G06F 9/453* (2018.02);

(Continued)

(58) Field of Classification Search
CPC . G06F 3/14; G06F 3/017; G06F 40/20; G06F 40/40; G06F 9/453; A61B 5/0022; A61B 5/02416; A61B 5/6893; G06T 7/0012; G06T 2207/20081; G06T 2207/30268; G06V 10/774; G06V 20/597; G06V 40/28; G02B 27/0101
See application file for complete search history.

(56) References Cited

U.S. PATENT DOCUMENTS

| | | |
|---|---|---|
| 7,060,343 B2 | 6/2006 | Freeman |
| 8,188,846 B2 | 5/2012 | Cooper et al. |

(Continued)

OTHER PUBLICATIONS

Envisics, "We redefine the way people see and interact with the world," URL: https://envisics.com/#welcome.

(Continued)

*Primary Examiner* — Grant Sitta
(74) *Attorney, Agent, or Firm* — Leydig, Voit & Mayer, Ltd.

(57) ABSTRACT

A system includes a heads up display (HUD) device for a vehicle, a cloud provisioned computing system, and one or more service provider devices is provided. The HUD device is configured to obtain biometric feedback data of a user; input the biometric feedback data to a remote photoplethysmography (rPPG) model to determine biometric condition data of the user; and generate an output for the user. The cloud provisioned computing system is configured to input a prompt to a machine learning-artificial intelligence (ML-AI) language model to determine a service provider system and provide to a common interface a request for service provider data; receive the service provider data; and provide the control signal to the HUD. The service provider device is configured to receive the request; determine the service provider data associated with the request; and provide the service provider data.

20 Claims, 8 Drawing Sheets

(51) Int. Cl.

| | | |
|---|---|---|
| *G06F 9/451* | (2018.01) | |
| *G06F 40/20* | (2020.01) | |
| *G06F 40/40* | (2020.01) | |
| *G06T 7/00* | (2017.01) | |
| *G06V 10/774* | (2022.01) | |
| *G06V 20/59* | (2022.01) | |
| *G06V 40/20* | (2022.01) | |

(52) U.S. Cl.

CPC ............... *G06T 2207/20081* (2013.01); *G06T 2207/30268* (2013.01)

(56) References Cited

U.S. PATENT DOCUMENTS

| | | | |
|---|---|---|---|
| 8,412,413 B1 | 4/2013 | Stark et al. | |
| 8,725,311 B1 | 5/2014 | Breed | |
| 9,129,505 B2 | 9/2015 | Breed et al. | |
| 9,317,983 B2 | 4/2016 | Ricci | |
| 9,399,430 B2 | 7/2016 | Kirsch et al. | |
| 9,460,601 B2 | 10/2016 | Mimar | |
| 10,065,574 B2 | 9/2018 | Tiryaki | |
| 10,430,556 B2 | 10/2019 | Mccauley et al. | |
| 10,591,738 B2 | 3/2020 | Svarichevsky et al. | |
| 10,729,378 B2 | 8/2020 | Lerner | |
| 10,754,152 B2 | 8/2020 | Arndt et al. | |
| 11,072,311 B2 * | 7/2021 | Luchner | G07C 9/25 |
| 11,259,710 B2 | 3/2022 | Mansour et al. | |
| 11,311,220 B1 * | 4/2022 | Al-Saggaf | A61B 5/165 |
| 11,341,671 B2 | 5/2022 | Lu et al. | |
| 11,355,241 B2 * | 6/2022 | Lassoued | G16H 20/00 |
| 11,645,856 B2 | 5/2023 | Lynam | |
| 11,780,372 B2 | 10/2023 | Sobecki et al. | |
| 11,823,468 B2 | 11/2023 | Woo | |
| 11,851,080 B2 | 12/2023 | Sobecki et al. | |
| 11,930,264 B2 | 3/2024 | Conger et al. | |
| 11,951,993 B2 | 4/2024 | Lu | |
| 12,056,148 B2 * | 8/2024 | Gleason | G16H 10/60 |
| 12,364,439 B2 * | 7/2025 | Wu | A61B 5/0816 |
| 12,423,088 B1 * | 9/2025 | Hwang | G06F 8/65 |
| 2002/0126876 A1 | 9/2002 | Paul et al. | |
| 2010/0292886 A1 | 11/2010 | Szczerba et al. | |
| 2017/0274906 A1 | 9/2017 | Hassan et al. | |
| 2019/0357834 A1 | 11/2019 | Aarts et al. | |
| 2021/0142903 A1 * | 5/2021 | Mason | G16H 20/30 |
| 2021/0223864 A1 * | 7/2021 | Forsland | G06N 5/02 |
| 2021/0370064 A1 * | 12/2021 | Murphy | G06N 3/0442 |
| 2022/0313077 A1 * | 10/2022 | Singh | A61B 3/14 |
| 2022/0401004 A1 * | 12/2022 | Othmane | A61B 5/7246 |
| 2023/0242124 A1 | 8/2023 | Lu | |
| 2024/0023816 A1 * | 1/2024 | Shouldice | A61B 5/0205 |
| 2024/0029879 A1 * | 1/2024 | Corlett | G16H 80/00 |
| 2024/0112337 A1 * | 4/2024 | Wacquant | G06V 20/52 |
| 2024/0312625 A1 * | 9/2024 | Bautista | G16H 20/00 |
| 2024/0326831 A1 * | 10/2024 | Bakhchina | G06V 20/597 |
| 2024/0347058 A1 * | 10/2024 | Rossi | G10L 13/08 |
| 2025/0166409 A1 * | 5/2025 | Jeon | G06V 40/15 |
| 2025/0306679 A1 * | 10/2025 | Kurfirst | G06F 3/015 |

OTHER PUBLICATIONS

Anura, "Take a selfie, know your healthie!" Mobile application on App Store and Google play, URL: https://www.nuralogix.ai/.

AI Nexus, "Good Health in the Palm of Your Hand," URL:https://www.ainexushealthcare.com/.

Haugg et al., "GRGB rPPG: An Efficient Low-Complexity Remote Photoplethysmography-Based Algorithm for Heart Rate Estimation," National Library of Medicine (Feb. 2023). URL:https://pubmed.ncbi.nlm.nih.gov/36829737/#:~:text=Remote%20photoplethysmography%20(rPPG)%20is%20a.introduced%20in%20the20existing%20literature.

Github-Ubicomplab, rPPG-Toolbox: Deep Remote PPG Toolbox, URL: https://github.com/ubicomplab/rPPG-Toolbox.

Hu et al., "rPPG-Based Heart Rate Estimation Using Spatial-Temporal Attention Network," IEEE Xplore, IEEE Transactions on Cognitive and Developmental Systems, vol. 14, Issue 4 (Dec. 2022). URL: https://Ieeexplore.ieee.org/document/9627878.

* cited by examiner

202

Bus

Processor ~ 204

ROM ~ 206

RAM ~ 208

Storage ~ 210

Network Interface ~ 212

200

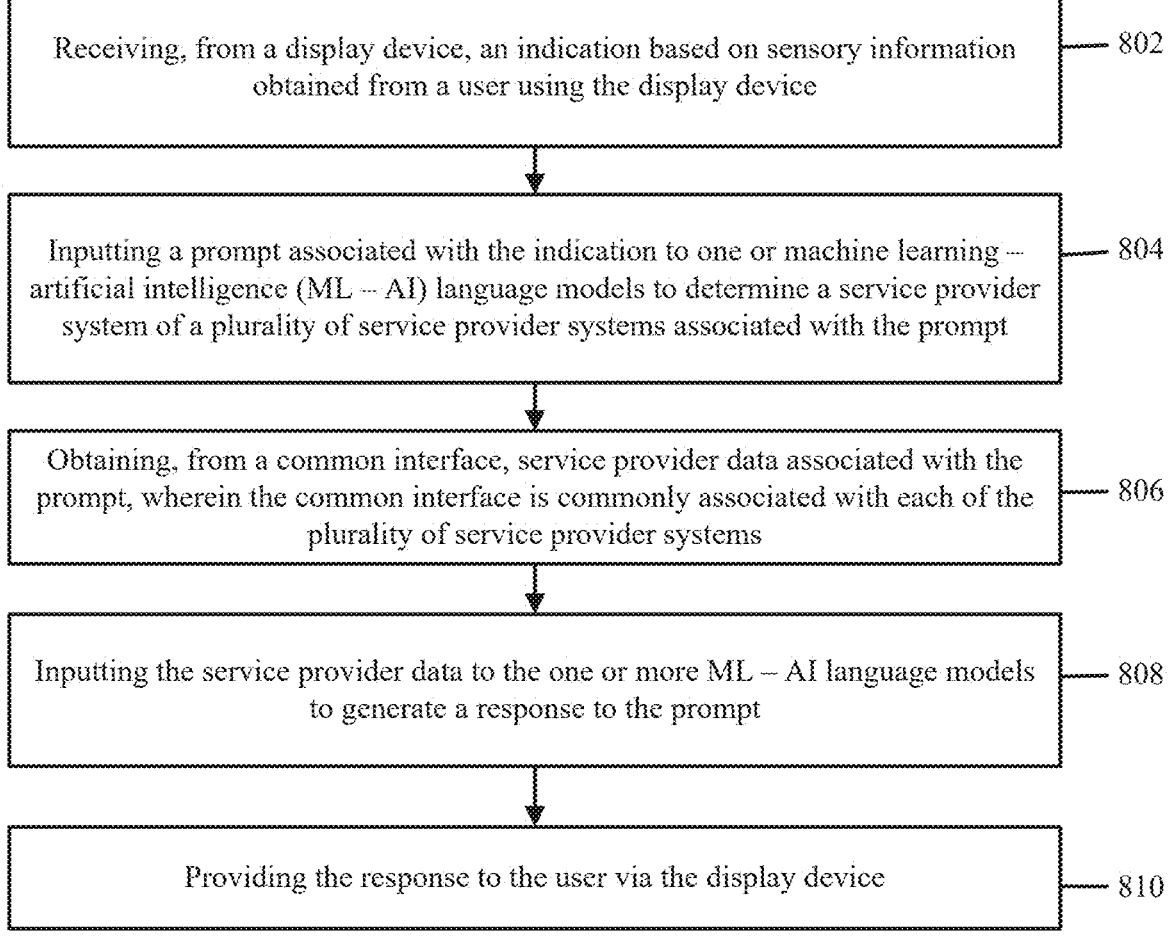

Receiving, from a display device, an indication based on sensory information obtained from a user using the display device — 802

Inputting a prompt associated with the indication to one or machine learning – artificial intelligence (ML – AI) language models to determine a service provider system of a plurality of service provider systems associated with the prompt — 804

Obtaining, from a common interface, service provider data associated with the prompt, wherein the common interface is commonly associated with each of the plurality of service provider systems — 806

Inputting the service provider data to the one or more ML – AI language models to generate a response to the prompt — 808

Providing the response to the user via the display device — 810

METHODS AND SYSTEMS FOR VIRTUAL ASSISTANCE USING A DEVICE

BACKGROUND

User assistance systems, such as driver assistance systems, may operate to capture images of a user and may process the captured image data to monitor the user or occupants of the vehicle. The assistance systems may receive image data from one or more cameras and provide an output to a display device for displaying images representative of the captured image data. For example, vital signs of a person, for example the heart rate, heart rate variability, the respiration rate, or the blood oxygen saturation, which may serve as indicators of the current state of a person and as a potential predictor of serious medical events, may be monitored by capturing images of a user and providing the images to a remote photoplethysmography (rPPG) model. These assistance systems may alert the user of anomalous vital signs based on an output of the rPPG model. However, these assistance systems typically fail to help the user address or respond to the anomalous vital signs. Accordingly, there remains a technical need to aid a user when addressing and/or resolving personal and/or biometric conditions experienced by a user.

SUMMARY

In some examples, the present application provides a method and system for providing virtual assistance to a user. For example, a heads-up display (HUD) device may obtain biometric feedback from a user and use one or more biometric detection models, such as one or more rPPG models and/or humidity models, to determine that the user has a biometric condition (e.g., elevated heart rate). The HUD device may provide an input to one or more virtual assistant models based on the biometric condition and use the one or more virtual assistant models to determine a further action that should be taken, such as refilling a prescription for the user's heart medication. The HUD device may provide a request for further information to an enterprise computing system, and the enterprise computing system may determine that a further service system (e.g., a pharmacy's system) contains information on the availability and location of the user's prescription. The enterprise computing system may obtain the data associated with the request from the further service system, and provide the obtained data to the one or more virtual assistant models of the HUD device. The HUD device may then use the virtual assistant models to generate a response to the user providing information on where the prescription may be collected and offering to update the navigation of a vehicle of the user to navigate to this location.

In one aspect a system comprises a HUD device for a vehicle, a cloud provisioned computing system, and one or more service provider devices. The HUD device comprises one or more biometric sensors and one or more sensory output devices. The HUD device is configured to obtain biometric feedback data of a user using the one or more biometric sensors; input the biometric feedback data to one or more rPPG models to determine biometric condition data of the user; provide the biometric condition data from the vehicle to a cloud provisioned computing system; and generate an output for the user, using the one or more sensory output devices, based on a control signal received from the cloud provisioned computing system. The cloud provisioned computing system is configured to input a prompt associated with the received biometric condition data to one or more machine learning-artificial intelligence (ML-AI) language models to determine one or more service provider systems associated with the received biometric condition data and provide to a common interface a request for service provider data from the one or more service provider systems; receive, from the one or more service provider system, the service provider data associated with the request; and provide the control signal to the HUD based on the service provider data. The one or more service provider devices comprise the one or more service provider systems, and the one or more service provider devices are configured to receive, from the cloud provisioned computing system, the request; determine, based on the request and using a service provider dataset associated with the service provider system, the service provider data associated with the request; and provide, to the cloud provisioned computing system, the service provider data.

Examples may include one of the following features, or any combination thereof. For instance, in some examples of the system, the one or more biometric sensors comprise an imaging device, the biometric feedback data comprises one or more images of the user obtained using the imaging device, and inputting the biometric feedback data to the one or more rPPG models further comprises inputting the one or more images of the user to the one or more rPPG models to determine the biometric condition data of the user based on a physiological trait of the user.

In some instances, the HUD device further comprises one or more assistant ML-AI language models, and the HUD device is further configured to: input, to one or more assistant ML-AI language models, the biometric condition data to determine that the biometric condition data is actionable; provide, to the user and from the one or more assistant ML-AI language models, a confirmation request for the user based on determining the biometric condition data is actionable, where the confirmation request requests a consent from the user to provide the biometric condition data from the vehicle to the cloud provisioned computing system; obtain, from the user, the consent and provide the consent to the one or more assistant ML-AI language models; and provide, by the one or more assistant ML-AI language models, the biometric condition data and the consent from the vehicle to a cloud provisioned computing system. The cloud provisioned computing system is further configured to input the prompt associated with the received biometric condition data to the one or more ML-AI language models based on receiving the consent from the HUD device.

In some variations, obtaining, from the user, the consent further comprises obtaining, from the user, a gesture performed by the user. The gesture represents the consent of the user.

In some examples, the one or more assistant ML-AI language models are trained based on gesture training data, and the gesture training data comprises a plurality of gestures for a user to perform associated with a meaning of each gesture of the plurality of gestures.

In some instances, generating the output for the user using the one or more sensory output devices further comprises projecting the output onto a surface external to the HUD device.

In some variations, the HUD device is further configured to provide, to a vehicle device, a second control signal to generate a second output associated with the output generated by the HUD device.

In some examples, the HUD device is further configured to obtain, from a wearable device, further biometric feedback data associated with the biometric feedback data. Inputting the biometric feedback data to the one or more rPPG models further comprises: inputting the biometric feedback data and the further biometric feedback data to the one or more rPPG models to determine the biometric condition data of the user.

In some instances, the HUD device is further configured to obtain a plurality of instances of biometric feedback data, each instance of biometric feedback data is obtained at a scheduled time interval, and the biometric feedback data is obtained at one of the scheduled time intervals.

In some variations, the cloud provisioned computing system comprises the one or more rPPG models, and inputting the biometric feedback data to the one or more rPPG models further comprises providing, to the cloud provisioned computing system, the biometric feedback data and a direction to input, by the cloud provisioned computing system, the biometric feedback data to the one or more rPPG models. The HUD is further configured to receive, from the cloud provisioned computing system, the biometric condition data of the user.

In another aspect, a method is provided. The method comprises receiving, from a display device, an indication based on sensory information obtained from a user using the display device; inputting a prompt associated with the indication to one or more ML-AI language models to determine a service provider system of a plurality of service provider systems associated with the prompt; obtaining, from a common interface, service provider data associated with the prompt, where the common interface is commonly associated with each of the plurality of service provider systems; inputting the service provider data to the one or more ML-AI language models to generate a response to the prompt; and providing the response to the user via the display device.

Examples may include one of the following features, or any combination thereof. For instance, in some examples of the method, the sensory information comprises a consent from the user associated with inputting the prompt to the one or more ML-AI language models.

In some instances, the prompt is based on the indication, and the method further comprises providing, to the display device, a confirmation request based on determining an actionable status and the confirmation request requests the consent from the user associated with inputting the prompt to the one or more ML-AI language models. Receiving, from the display device, the indication further comprises obtaining, by the display device, the consent from the user; and generating, by the display device, the indication based on the obtained consent from the user, and inputting the prompt to the one or more ML-AI language models further comprises inputting the prompt to the one or more ML-AI models based on obtaining the consent of the user.

In some examples, the sensory information comprises biometric feedback data and the method further comprises inputting the indication to one or more ML-AI biometric detection models to determine biometric condition data of the user; and generating the prompt based on the biometric condition data of the user. The prompt comprises a request for the service provider data associated with the biometric condition.

In some variations, generating the prompt further comprises inputting the biometric condition data of the user to a prompt engine to generate the prompt based on selecting, by the prompt engine, a first prompt template of a plurality of prompt templates of the prompt engine. The first prompt template is stored with an association to the determined biometric condition data.

In some instances, the sensory information comprises biometric feedback data and a consent from the user, and the indication is generated based on the biometric feedback data and the consent from the user associated with inputting the prompt to the one or more ML-AI language models and the prompt is associated with the biometric condition data of the user. Receiving, from the display device, the indication further comprises receiving, from the display device, the biometric feedback data, and the method further comprises inputting the biometric feedback data to one or more ML-AI biometric detection models to determine biometric condition data of the user; providing, to the display device, a confirmation request based on determining the biometric condition data is actionable, where the confirmation request requests the consent from the user associated with inputting the prompt to the one or more ML-AI language models; and generating the prompt based on the biometric condition data of the user. Inputting the prompt to the one or more ML-AI language models further comprises inputting the prompt to the one or more ML-AI models based on receiving the consent of the user.

In some examples, obtaining, from the common interface, the service provider data further comprises accessing, by the common interface, a first service feature dataset of a first service provider system of the plurality of service provider systems; and obtaining, from the first service feature dataset and by the common interface, first service provider data associated with the prompt. Inputting the service provider data to the one or more ML-AI language models further comprises inputting the first service provider data to the one or more ML-AI language models.

In some variations, obtaining, from the common interface, the service provider data further comprises providing, by the common interface, the first service provider data to a second service provider system of the plurality of service provider systems; accessing, by the common interface, a second service feature dataset of the second service provider system; and obtaining, from the second service feature dataset and by the common interface, second service provider data associated with the prompt and the first service provider data. Inputting the service provider data to the one or more ML-AI language models further comprises inputting the first service provider and the second service provider data to the one or more ML-AI language models.

In some instances, the method further comprises providing, to the display device, a further request to the user based on the obtained service provider data requesting a consent of the user to provide the first service provider data to the second service provider system; and receiving, from the display device, the consent of the user to provide the first service provider data to the second service provider system. Providing, by the common interface, the first service provider data to the second service provider system is based on receiving the consent of the user to provide the first service provider data to the second service provider system.

In another aspect, a non-transitory computer-readable medium is provided. The non-transitory, computer-readable medium has processor-executable instructions stored thereon, wherein the processor-executable instructions, when executed, facilitate receiving, from a display device, an indication based on sensory information obtained from a user using the display device; inputting a prompt associated with the indication to one or ML-AI language models to determine a service provider system of a plurality of service provider systems associated with the prompt; obtaining, from a common interface, service provider data associated with the prompt, where the common interface is commonly associated with each of the plurality of service provider systems; inputting the service provider data to the one or more ML-AI language models to generate a response to the prompt; and providing the response to the user via the display device.

BRIEF DESCRIPTION OF THE DRAWINGS

The subject technology will be described in even greater detail below based on the exemplary figures, but is not limited to the examples. All features described and/or illustrated herein can be used alone or combined in different combinations. The features and advantages of various examples will become apparent by reading the following detailed description with reference to the attached drawings which illustrate the following:

FIG. 8 is a depiction of an exemplary process for providing a response to an indication of a user via a display device in accordance with one or more examples of the present application.

DETAILED DESCRIPTION

Examples of the presented application will now be described more fully hereinafter with reference to the accompanying FIGs., in which some, but not all, examples of the application are shown. Indeed, the application may be exemplified in different forms and should not be construed as limited to the examples set forth herein; rather, these examples are provided so that the application will satisfy applicable legal requirements. Where possible, any terms expressed in the singular form herein are meant to also include the plural form and vice versa, unless explicitly stated otherwise. Also, as used herein, the term "a" and/or "an" shall mean "one or more" even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on."

Figure 1:
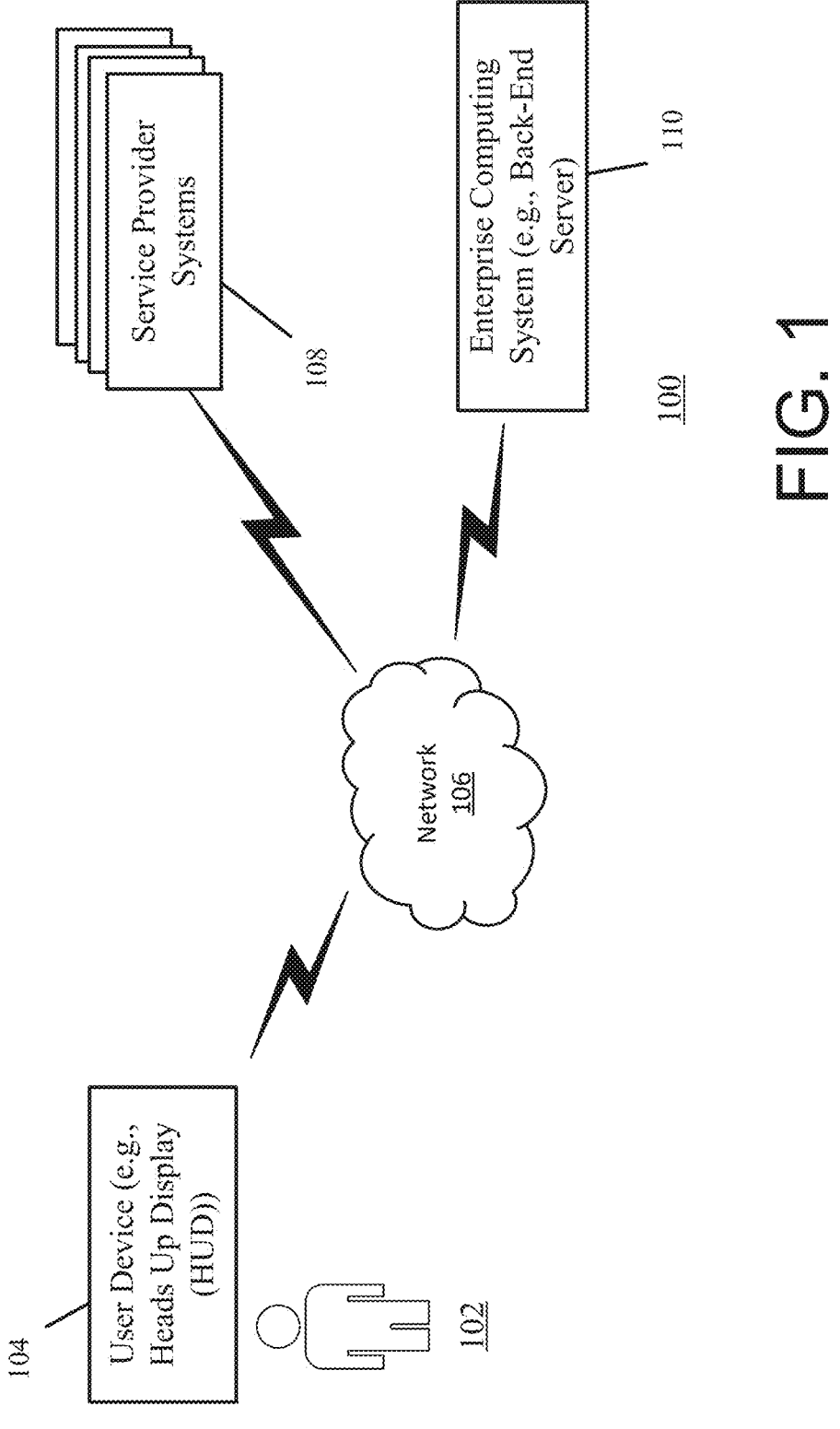
FIG. 1 is a simplified block diagram depicting an exemplary virtual assistant environment in accordance with one or more examples of the present application.

Systems, methods, and computer program products are herein disclosed that use one or more display devices to obtain feedback (e.g., sensory, including biometric) from a user and provide a response to that feedback to the user. FIG. 1 is a simplified block diagram depicting an exemplary environment in accordance with an example of the present application. The environment 100 includes a user 102, and a user device 104 (e.g., a HUD), a network 106, one or more service provider systems 108, and an enterprise computing system 110. Although the entities within environment 100 may be described below and/or depicted in the FIGS. as being singular entities, it will be appreciated that the entities and functionalities discussed herein may be implemented by and/or include one or more entities.

The entities within the environment 100 such as the enterprise computing platform 108 and the user device 104 may be in communication with each other within the environment via network 106. The network 106 may be a global area network (GAN) such as the Internet, a wide area network (WAN), a local area network (LAN), or any other type of network or combination of networks. The network 106 may provide a wireline, wireless, or a combination of wireline and wireless communication between the entities within the environment 100. Additionally, the network 106 may support or include communication protocols such as WI-FI or BLUETOOTH.

The user 102 may be a person associated with a user device 104. The user 102 may be able to provide sensory information, such as gestures and oral information, to a user device 104. The user device 104 is and/or includes one or more HUD devices, computing devices, platforms, and/or systems that are configured to receive, obtain, generate, store, ingest, and/or otherwise process data such as sensory information (e.g., biometric feedback, user input). The user device 104 may further provide or transmit the data to another entity within environment 100 such as the enterprise computing system 110. In some examples, the user device 104 is and/or includes one or more HUD devices, computing devices, computing platforms, systems, servers, desktops, laptops, tablets, mobile devices (e.g., smartphone device, or other mobile device), or any other type of computing device that generally comprises one or more communication components, one or more processing components, and one or more memory components.

The user device 104 is are capable of performing tasks, functions, and/or other actions associated with an enterprise organization. For example, the user device 104 may be a HUD device that obtains sensory information from the user 102, generates one or more indications based on the sensory information, and provides the sensory information and/or indications (e.g., requests based on the sensory information) to the enterprise computing system 110. For instance, the user device 104 may obtain (e.g., sense, collect, receive, and/or track) biometric feedback from the user such as images indicating blood flow patterns and generate a biometric condition such as elevated heart rate. For example, the user device 104 may be deployed in a vehicle of the user 102 and obtain this information passively while user 102 drives the vehicle. The user device 104 may provide this sensory information and/or indication to the enterprise computing system 110 before or after requesting consent from the user 102 to provide the sensory information and/or indication. The user 102 may provide sensory information (e.g., a gesture or oral confirmation) that the user device 104 uses as input to generate an indication that the user consents to providing the sensory information and/or indication.

The one or more service provider system 108 and enterprise computing system 110 within environment 100 may be a computing platform that is associated with one or more enterprise organizations. The respective enterprise organization may be any type of corporation, company, organization, and/or other institution that provides a plurality of services. In some instances, the enterprise organization may own, operate, and/or be otherwise associated with a health-care service, a retail and/or pharmaceutical service, an insurance service, and/or other types of services. For instance, an individual (e.g., user 102) may be enrolled into multiple different services provided by the one or more service provider systems 108. For example, the individual may use a grocery pick-up service provided by the enterprise organization via a first service provider system 108, a prescription pick-up service provided by the enterprise organization via a second service provider system 108, an insurance service provided by the enterprise organization (e.g., the enterprise organization may provide insurance to the individual) via a third service provider system 108, a streaming service provided by the enterprise organization via a fourth service provider system 108, a healthcare service (e.g., care management and/or other types of health-care services) provided by the enterprise organization via a fifth service provider system 108, and/or other services provided by the enterprise organization via further service provider systems 108. Each of these service provider systems 108 may be associated with a different computing platform. In other words, each of the service provider systems 108 may operate, manage, and/or otherwise be associated with one or more services provided by the enterprise organization. In some instances, each of the computing platforms for the one or more service provider systems 108 may be associated with a single enterprise organization. In other instances, multiple enterprise organizations may be associated with the each of computing platforms for the one or more service provider systems 108.

While only four service provider systems 108 are shown, the environment 100 may include any number of service provider systems 108. For example, the enterprise organization may seek to acquire, merge, and/or partner with another enterprise organization that provides another service (e.g., a streaming service). Accordingly, the environment 100 may include a fifth service provider system 108 that provides the fifth service.

Each of the one or more service provider systems 108 includes one or more computing devices, computing platforms, cloud computing platforms, systems, servers, and/or other apparatuses capable of performing tasks, functions, and/or other actions for the enterprise organization. In some variations, the one or more service provider systems 108 may be implemented as engines, software functions, and/or applications. In other words, the functionalities of the one or more service provider systems 108 may be implemented as software instructions stored in storage (e.g., memory) and executed by one or more processors.

The enterprise computing platform 110 is a computing platform that is associated with an enterprise organization. The enterprise organization may be any type of corporation, company, organization, and/or other institution. In some instances, the enterprise organization may provide health, medical, retail, and/or other commercial services, and/or be otherwise be associated with providing multiple different services. For example, a user may request which retail location sells a certain product, whether and where their medical prescription is ready for collection, and/or if a nearby doctor has any availability in the near future. The enterprise organization may receive the user's requests and access one or more of the service provider systems related to each of the user's request, and their feature datasets, to provide an answer to the user's request.

The enterprise computing platform 110 may perform one or more tasks for the enterprise organization based on information from the one or more service provider systems 108 and/or user device 104. For example, the supervisor computing platform 110 may obtain sensory information and/or one or more indications from the user device 104, and provide and/or obtain service provider data from one or more of the service provider systems 108 and determine one or more responses based on the sensory information, one or more indications, and/or service provider data. For instance, the enterprise computing system 110 may use one or more ML-AI models, algorithms, and/or datasets (e.g., ML-AI models) to determine the one or more responses. Then, based on the responses, the enterprise computing system 110 may provide the responses and/or one or more control signals to the user device 104.

The enterprise computing system 110 includes one or more computing devices, computing platforms, systems, servers, and/or other apparatuses capable of performing tasks, functions, and/or other actions for the enterprise organization. The enterprise computing system 110 may be implemented using one or more computing platforms, devices, servers, and/or apparatuses. In some variations, the enterprise computing system 110 may be implemented as engines, software functions, and/or applications. In other words, the functionalities of the enterprise computing platform 108 may be implemented as software instructions stored in storage (e.g., memory) and executed by one or more processors.

Figure 2:
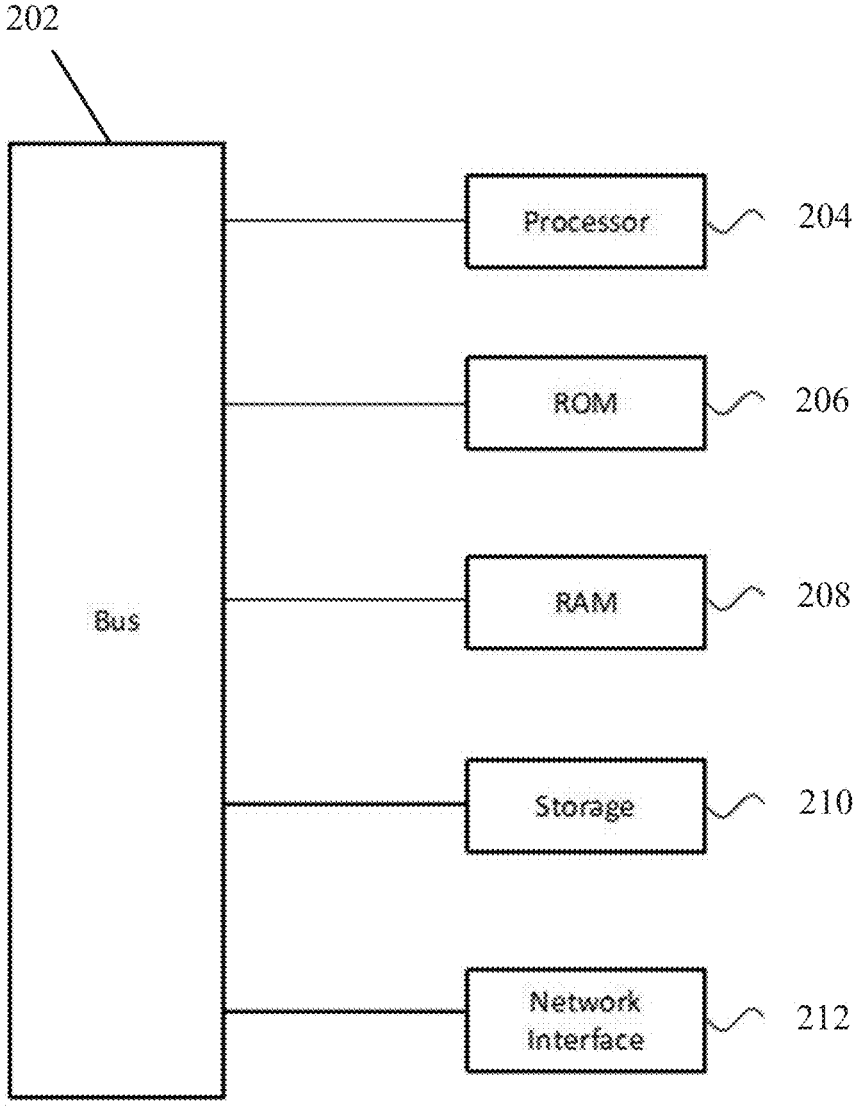
FIG. 2 is a simplified block diagram of one or more devices or systems within the exemplary environment of FIG. 1.

FIG. 2 is a block diagram of an exemplary system and/or device 200 within the environment 100. The device/system 200 includes a processor 204, such as a central processing unit (CPU), controller, and/or logic, that executes computer executable instructions for performing the functions, processes, and/or methods described herein. In some examples, the computer executable instructions are locally stored and accessed from a non-transitory computer readable medium, such as storage 210, which may be a hard drive or flash drive. Read Only Memory (ROM) 206 includes computer executable instructions for initializing the processor 204, while the random-access memory (RAM) 208 is the main memory for loading and processing instructions executed by the processor 204. The network interface 212 may connect to a wired network or cellular network and to a local area network or wide area network, such as the network 106. The device/system 200 may also include a bus 202 that connects the processor 204, ROM 206, RAM 208, storage 210, and/or the network interface 212. The components within the device/system 200 may use the bus 202 to communicate with each other. The components within the device/system 200 are merely exemplary and might not be inclusive of every component within the device/system 200. For example, as will be described below, the enterprise computing system 108 and the user device 104 may include some of the components within the device/system 200 and may also include further components such as one or more sensors and/or devices. Additionally, and/or alternatively, the device/system 200 may further include components that might not be included within every entity of environment 100.

Figure 3:
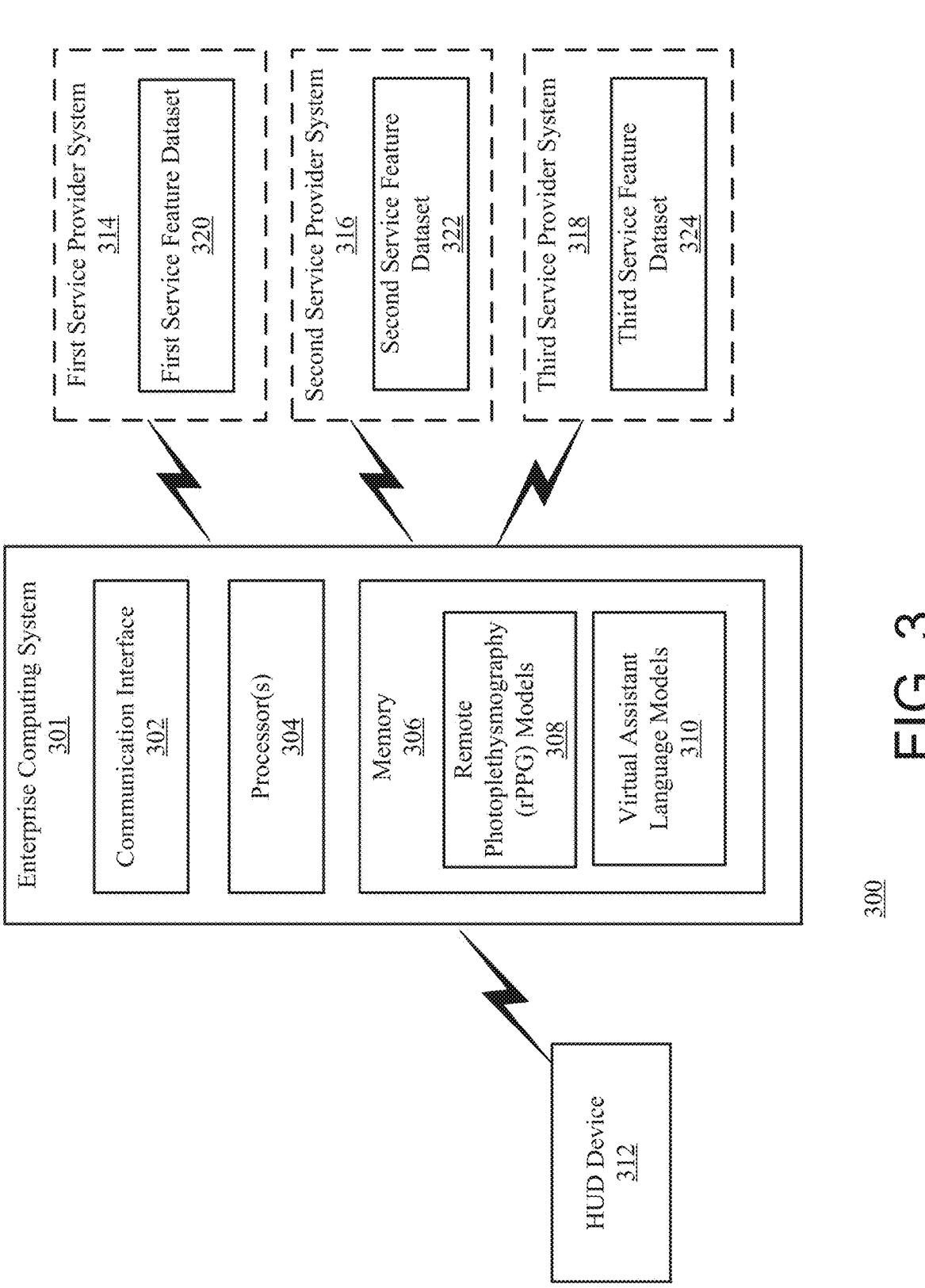
FIG. 3 is a simplified block diagram depicting an exemplary enterprise computing system providing the virtual assistant in accordance with one or more examples of the present application.

The enterprise computing system may receive sensory information and/or requests from the HUD device, provide and/or obtain service provider data from one or more service provider systems, determine a response to a user, and provide the response to the HUD device. An exemplary environment 300 for doing so is described in FIG. 3, which shows a simplified block diagram depicting an exemplary enterprise computing system providing the virtual assistant in accordance with one or more examples of the present application environment For example, as shown in FIG. 3, environment 300 may include an enterprise computing system 301, HUD device 312, and one or more service provider systems 314, 316, and 318, where any one of the service provider systems may be optional as indicated by the dashed box. The enterprise computing system 301 (e.g., similar to enterprise computing system 110) may communicate with a HUD device 312 (e.g., a user device such as user device 104, including a wearable device and/or smartphone capable of running an application providing for enterprise computing system 301) and/or the servers of an enterprise computing system 110. The enterprise computing system 301 may include a memory 306 including one or more rPPG models 308 (e.g., biometric machine learning-artificial intelligence (ML-AI) model) and/or one or more virtual assistant language models 310 (e.g., small language model (SLM), large language model (LLM), multi-modal language model (MMLM)). The enterprise computing system 301 may also use a communication interface 302 (e.g., an input/output device and/or an application programming interface (API)) to receive feedback and/or requests from the HUD device 312, and may use one or more processors 304 to input the feedback and/or requests to the one or more rPPG models 308 and/or virtual assistant language models 310 in memory 306 to generate an output requesting data from one or more service providers. Additionally, and/or alternatively, the HUD device 312 may provide, to the enterprise computing system 301 (e.g., a cloud provisioned computing system), the biometric feedback data and a direction to input the biometric feedback data to the one or more rPPG models. The enterprise computing system 301 may use the one or more processors 304 to provide the output to the communication interface 302. The enterprise computing system 301 may use the communication interface 302 to obtain data from one or more of the first service provider system 314, the second service provider system 316, and/or the third service provider system 318 associated with the request. For example, the generated output may direct the communication interface 302 to obtain data from the first service provider system 314 and/or the second service provider system 316, but not third service provider system 318 (e.g., the communication interface 302 may obtain data from one or more service provider systems based on the generated output). Each service provider system may include their own respective and separate service feature dataset (e.g., first service provider system 314 includes and/or maintains first service feature dataset 320 separate from second service provider system 316 including and/or maintain second service feature dataset 322). Additionally, and/or alternatively, different service provider systems may access different portions of a commonly shared feature dataset. For example, first service feature dataset 320 may be included in the same dataset as the third service feature dataset 324, but first service provider system 314 may access (e.g., utilize, maintain) first service feature dataset 320 as a different portion of the same dataset as the third service feature dataset 324, which is accessed by the third service provider system 318.

The enterprise computing system 301 may use the communication interface 302 to obtain data from one or more service feature dataset associated with the generated output and/or associated with the received feedback and/or requests from the HUD device. The enterprise computing system 301 may use the one or more processors 304 to input the obtained data to the one or more rPPG models 308 and/or virtual assistant language models 310 in memory 306 to generate a response to the user's feedback and/or request. The enterprise computing system 301 may use the one or more processors 304 to provide this response to the communication interface 302, and use the communication interface 302 to provide the response to the HUD device 312 in one or more forms. Additionally, and/or alternatively, the enterprise computing system 301 may use the communication interface 302 to provide the biometric condition data directly to the HUD device 312, alone or in combination with the response. For example, the communication interface 302 may provide a control signal providing text data for the user to read when displayed by the HUD device 312 and/or a control signal instructing the HUD device 312 to display the text. Additionally, and/or alternatively, the communication interface 302 may provide a control signal providing auditory data for the user to listen to when produced by the HUD device 312 and/or a control signal instructing the HID device 312 to produce the audio. Additionally, and/or alternatively, the communication interface 302 may provide a control signal (e.g., alone or in addition to another control signal) to an integrated system (e.g., navigation, calendar scheduling, emergency communications) data for use by an integrated system and/or the HUD device 312 to implement the integrated system data (e.g., update user's vehicle navigation, add an appointment to the user's calendar, and/or call emergency services).

The enterprise computing system (e.g., enterprise computing system 301) and/or the HUD device (e.g., HUD device 400) may use biometric detection models (e.g., rPPG models 308, biometric detection models 416) to determine biometric condition data. For example, an rPPG model (e.g., rPPG models 308) may use one or more types of input data (e.g., visible spectrum images, infrared images, blood pressure data) indicative of blood flow patterns such as subtle changes in the coloring of a user's face. Based on the determined blood flow patterns, the rPPG may generate a diagnosis of a biometric condition and/or data on which a diagnosis of a biometric condition may be based. For example, the HUD device (e.g., HUD device 312 and/or 400) may obtain a one or more images (e.g., a 30 second video) of a user's face using a vision imaging device (e.g., image capturing device 402) and, using one or more processors (e.g., HUD processor(s) 412), input the obtained one or more images to the rPPG model (e.g., rPPG models 308, biometric detection models 416) to determine the biometric condition data of the user based on a physiological trait (e.g., blood flow patterns indicated by the obtained one or more images) of the user. The vision imaging device may obtain (e.g., collect) these images without identifying the user, obtaining identifying characteristics of the user, and/or protected medical information. Based on the provided input, the rPPG model may output biometric condition data of the user (e.g., blood pressure, heart rate, normal or irregular blood flow indicative of arrhythmia or deviating from a user standard). The HUD device may then generate a response to the user based on the biometric condition data of the user, such as projecting onto a windshield or projection surface "possible motion sickness detected, passenger A." Additionally, and/or alternatively, obtaining the one or more images may be performed passively (e.g., at regular/scheduled time intervals), actively (e.g., upon request of the user), or a mix of the two (e.g., upon noticing the user or passenger unintentionally produce a specific sound or perform a specific gesture).

Additionally, and/or alternatively, the HUD device 312 may provide the obtained one or more images to the enterprise computing system 301, and the enterprise computing system 301 may input the obtained one or more images to the one or more rPPG models 308. For example, the enterprise computing system (e.g., enterprise computing system 301) may receive the obtained one or more images from the HUD device (e.g., HUD device 312 and/or 400) and, using one or more processors (e.g., processor(s) 304), provide the obtained one or more images to the rPPG model (e.g., rPPG models 308). When no personal identifying information is obtained from the user in the one or more images, the HUD device may not be required to request consent to provide the obtained one or more images to the enterprise computing system. Based on the provided input, the enterprise computing system 301 may use the rPPG model to generate biometric condition data (e.g., blood pressure, heart rate, normal or irregular blood flow indicative of arrhythmia) of the user.

The enterprise computing system (e.g., enterprise computing system 301) and/or the HUD device (e.g., HUD device 400) may train biometric detection models (e.g., rPPG models 308, biometric detection models 416) using user specific and/or generalized data. For instance, the enterprise computing system may train the one or more rPPG models using a generalized data set including images and biometric data collected from multiple different users and/or a specific data set including images and biometric data collected from the user (e.g., user 102). Additionally, and/or alternatively, the enterprise computing system may train one or more heart rate detection models using a generalized data set including heart rate patterns and biometric data collected from multiple different users and/or a specific data set including heart rate patterns and biometric data collected from the user (e.g., user 102). Additionally, and/or alternatively, the enterprise computing system may train one or more humidity and/or visual detection models using a generalized data set including measured water vapor around the HUD and biometric data collected from multiple different users and/or a specific data set including example water vapor levels generated by the user and biometric data collected from the user (e.g., user 102).

Additionally, and/or alternatively, the enterprise computing system (e.g., enterprise computing system 301) and/or the HUD device (e.g., HUD device 400) may receive pretrained rPPG models and/or biometric condition models training one generalized data. Additionally, and/or alternatively, the HUD device (e.g., HUD device 400) may receive pretrained biometric condition models (e.g., biometric detection models 416) from the enterprise computing system (e.g., enterprise computing system 301), which has performed training of the biometric condition models using user specific and/or generalized data. Additionally, and/or alternatively, the rPPG model may be trained using supervised or unsupervised training and/or data.

The one or more virtual assistant models (e.g., virtual assistant language models 310, virtual assistant models 418, virtual assistant 708) may determine that a request and/or a biometric condition is actionable (e.g., should be addressed) and perform one or more functions based on one or more types of input data. For example, the one or more virtual assistant models may include a multi-modal language model (MMLM) capable of receiving images, audio, text, and/or biometric data as input data and processing the input data to generate an output. The MMLM may receive the image, audio, and/or text data simultaneously, and the MMLM may be trained based on a dataset (e.g., a single dataset) including each of the image, audio, and/or text data. Additionally, and/or alternatively, the one or more virtual assistant models may include a plurality of models (e.g., language models), wherein each virtual model receives a designated input type (e.g., images, audio, text, or biometric data) and processes the respective data type to generate an output. Additionally, and/or alternatively, a common virtual assistant model may receive the outputs of each respective virtual assistant model (e.g., each output being generated in the same type such as text) and generate an output based on each output of the respective virtual assistant models. For instance, each virtual assistant model may operate independently and provide an output to the common virtual assistant model without requiring any layers (e.g., decoders) to be shared between the virtual assistant models. Additionally, and/or alternatively, the one or more virtual assistant models may include a prompt engine for generating prompts for the virtual assistant models, and that prompt engine may be trained together or separately from the one or more virtual assistant models. For instance, the HUD and/or enterprise computing system may input, to the one or more virtual assistant models, an image of a user's face and/or a user's hand performing a gesture with audio data based on a user's spoken request to the HUD. The HUD and/or enterprise computing system may use the one or more virtual assistant models to generate an output, such as a determination of a user's status (e.g., actionable, in need of aid), a response (e.g., confirmation request) to the user based on determining the biometric condition is actionable (e.g., displaying text via the HUD reading "it appears one of the users may be carsick. May I update navigation to a location that provide aid?"), and/or a determination of a further action (e.g., determining that and/or which service system should be contacted to schedule an appointment).

The HUD and/or enterprise computing system may train the one or more virtual assistant models using one or more sets of training data. For instance, the HUD and/or enterprise computing system may train the virtual assistant models by inputting a set of training data including data obtained from the user, and when using a supervised training data set, associating (e.g., via labeling) a user's input with a user-selected output (e.g., a specific audio file of the user "update navigation" indicating an action for the virtual assistant model to take, such as updating navigation data of the user's vehicle) to train the models to perform the user-selected output based on receiving the user's input. Additionally, and/or alternatively, the HUD and/or enterprise computing system may train the one or more virtual assistant models by inputting a supervised set of training data including data obtained from the user associating a user's input with a standard output (e.g., a user-selected voice prompt indicating the virtual assistant model should direct the HUD to obtain images of the user's face for inputting to the one or more rPPG models). Additionally, and/or alternatively, the HUD and/or enterprise computing system may train the one or more virtual assistant models by inputting a set of training data including input data obtained from entities other than the user, and when using a supervised training data set, associating the input data with a standard or user-selected output. Additionally, and/or alternatively, the HUD and/or enterprise computing system may train the one or more virtual assistant models based on training data provided and managed exclusively by the enterprise computing system (e.g., enterprise computing system 608). For example, the HUD and/or enterprise computing system may input training data including a text prompt, from the user and/or generate using a prompt engine or further virtual assistant model, reading "please call a driver to pick me up and take me to the hospital" and association to an output of providing the user's location, hospitals location, and/or payment information to a service provider (e.g., the service system of the driver) and requesting a driver based thereon.

Additionally, and/or alternatively, the one or more virtual assistant language models may utilize gesture recognition technology that allows the virtual assistant language model to receive inputs based on user's hand gestures (e.g., obtained by the HUD), which may reduce the need for physical buttons or touchscreens. For example, the one or more virtual assistant language models may include an MMLM. The virtual assistant language model (e.g., an MMLM) may output a communication to the user (e.g., producing audio or displaying text using the HUD) that new navigation information has been received, and request that the user provide their consent for the virtual assistant language model to update the user's navigation information. The MMLM may receive (e.g., from a HUD or enterprise computing system) as an input one or more images and/or biometric sensor data (e.g., heat map of a user's hand or head) in response to the request provided to the user. The images and/or biometric data may show a static gesture performed (e.g., thumbs up) or a motion performed by the user (e.g., nodding head or waving hand). The MMLM may utilize one or more tokenizer layers for each type of input (e.g., images, biometric data) or one or more general tokenizer layers, and provide the output of the one or more tokenizer layers to one or more encoders for each tokenizer layer or one or more general encoder layers to generate vector embeddings for the input images and/or biometric sensor data. After the MMLM determines the meaning of the performed gesture, such as the performed gesture meaning that the user consents to an action or request, the MMLM may perform the action associated with the gesture, such as updating the navigation.

Additionally, and/or alternatively, the one or more virtual assistant language models may be trained to recognize a performed gesture based on user-specific training data or based on generalized training data. For instance, the virtual assistant language model may be trained on gesture training data including images and/or biometric sensor data obtained of the user performing specific gestures, and when using a supervised training data set, associated with the meaning of those gestures. The user may select the specific gestures and their associated meaning. Additionally, and/or alternatively, the training data may be a standardized training data including images and/or biometric sensor data obtained of the user and/or other entities performing specific gestures. For example, the one or more virtual assistant language models be trained to identify a snap of the fingers (e.g., with or without complimentary audio data of the snap) as a command to open a home screen or navigation window and/or a nod of the head as consent to perform an action based on training data including these gestures and associated meanings.

Additionally, and/or alternatively, the one or more virtual assistant models may be trained to engage in conversation with the driver. For instance, the HUD and/or enterprise computing system may input training data to the one or more virtual assistant models including text and/or audio based data (e.g., books, research papers, internet articles, films)

and conducting supervised and/or unsupervised training of the inferences (e.g., the predicted next word) of the one or more virtual assistant models. For example, the HUD and/or enterprise computing system may provide labeled training data sets to the one or more virtual assistant models to influence (e.g., personalize) how the one or more virtual assistant models engage in conversation. Additionally, and/or alternatively, the HUD and/or enterprise computing system may provide unlabeled training data sets to the one or more virtual assistant models to allow the one or more virtual assistant models to generate more independent outputs. For example, the HUD and/or enterprise computing system may train the one or more virtual assistant model to provide opinions, information, and/or data associated with a user's input (e.g., question or comment) provided to the one or more virtual assistant models.

Additionally, and/or alternatively, the one or more virtual assistant models may be trained to provide gamification elements to the driver. For example, the HUD and/or enterprise computing system may input a set of training data to the one or more virtual assistant models including tasks performed by the user and/or the vehicle (e.g., safe braking practices while driving, drinking water, signaling for turns) associated with a window to generate on the HUD interface indicating the user has earned driving points or discounts at an enterprise location.

Additionally, and/or alternatively, the one or more virtual assistant models may generate an avatar and communicate with the user using the avatar. The avatar may be distinct from an avatar of another user, and may be customized based on user preferences (e.g., language, age, race) to provide accessibility and comfort to the user. For instance, the HUD and/or enterprise computing system may generate an avatar (e.g., personification) that provides the outputs of the one or more virtual assistant models to the user or other entities. For example, the HUD may display an avatar when engaging in conversation with the user (e.g., while driving) as described above. The user may then exit their vehicle and open an application on a device (e.g., smartphone, wearable device) that displays the avatar and continues to obtain input data from the user and generate outputs to the user. The user may then enter a service provider facility (e.g., a doctor's office) and bring the avatar with them via their device. Additionally, and/or alternatively, the avatar may be displayed at the service provider facility for the user to interact with (e.g., provide input data and obtain outputs from the avatar). For example, the avatar may be displayed at the service provider facility, and/or further facilities, based on the same one or more virtual assistant models of the user (e.g., the avatar displayed on the user device), and obtain and/or provide input data while displayed at the service provider facility. The user may then allow the avatar to engage in conversation and/or perform tasks for the user with a service provider employee, such as obtaining input data (e.g., from the user and/or the employee) based on a questions from a service provider employee (e.g., a doctor's question to the user) and generate outputs to the user and/or doctor (e.g., answering on behalf of the user, directing the user to a product in the service provider facility). For instance, the avatar may access a service provider system and/or memory to retrieve a managed data set including medical information of the user (e.g., medical records, healthcare information) based on the received input data and provide the medical information or a response based on the medical information as an output to the user and/or doctor. Additionally, and/or alternatively, the avatar may provide explanations to a user based on a received input (e.g., explaining how billing will be handled for a given procedure). In this way, the one or more virtual assistant models may provide an advocate service for the user.

The one or more virtual assistant models may manage and/or access a data set for assisting the user. For instance, the HUD and/or enterprise computing system may access a user data set in memory (e.g., memory 306, 414) using the one or more virtual assistant models. Additionally, and/or alternatively, the one or more virtual assistant models may access the data set provided by a service provider system (e.g., first service provider system 610) of the enterprise network (e.g., enterprise network 606). The user data set may include data associated with the user (e.g., medical records of the user, health insurance provider information, residence location) provided by the user or that the user has authorized the one or more virtual assistant models to obtain and/or store, and the one or more virtual assistant models may update this data set based on receiving additional input data (e.g., new or updated medical records). For instance, the one or more virtual assistant models may be distinct to the user and manage the user data, and the one or more virtual assistant models may adjust themselves based on the received input data and prompts to accommodate the received (e.g., new) input data. The user data set may include data entirely from the enterprise network (e.g., enterprise computing system 608 and service provider systems 610, 612) and/or temporary data such as the physical store layout and inventory locations of a service provider facility (e.g., of a third party service provider system 614) in which the avatar is displayed to direct users within the facility. The one or more virtual assistant models may obtain this temporary data from the service provider based on being displayed (e.g., projected) in a facility of the service provider. The temporary data may then be removed from the data set upon no longer being displayed in the facility of the service provider.

The enterprise computing system 301 includes one or more computing devices, computing platforms, systems, servers, and/or other apparatuses capable of performing tasks, functions, and/or other actions for the enterprise organization. The enterprise computing system 301 may be implemented using one or more computing platforms, devices, servers, and/or apparatuses. In some variations, the enterprise computing system 301 may be implemented as engines, software functions, and/or applications. In other words, the functionalities of the enterprise computing system 301 may be implemented as software instructions stored in storage (e.g., memory) and executed by one or more processors.

Figure 4:
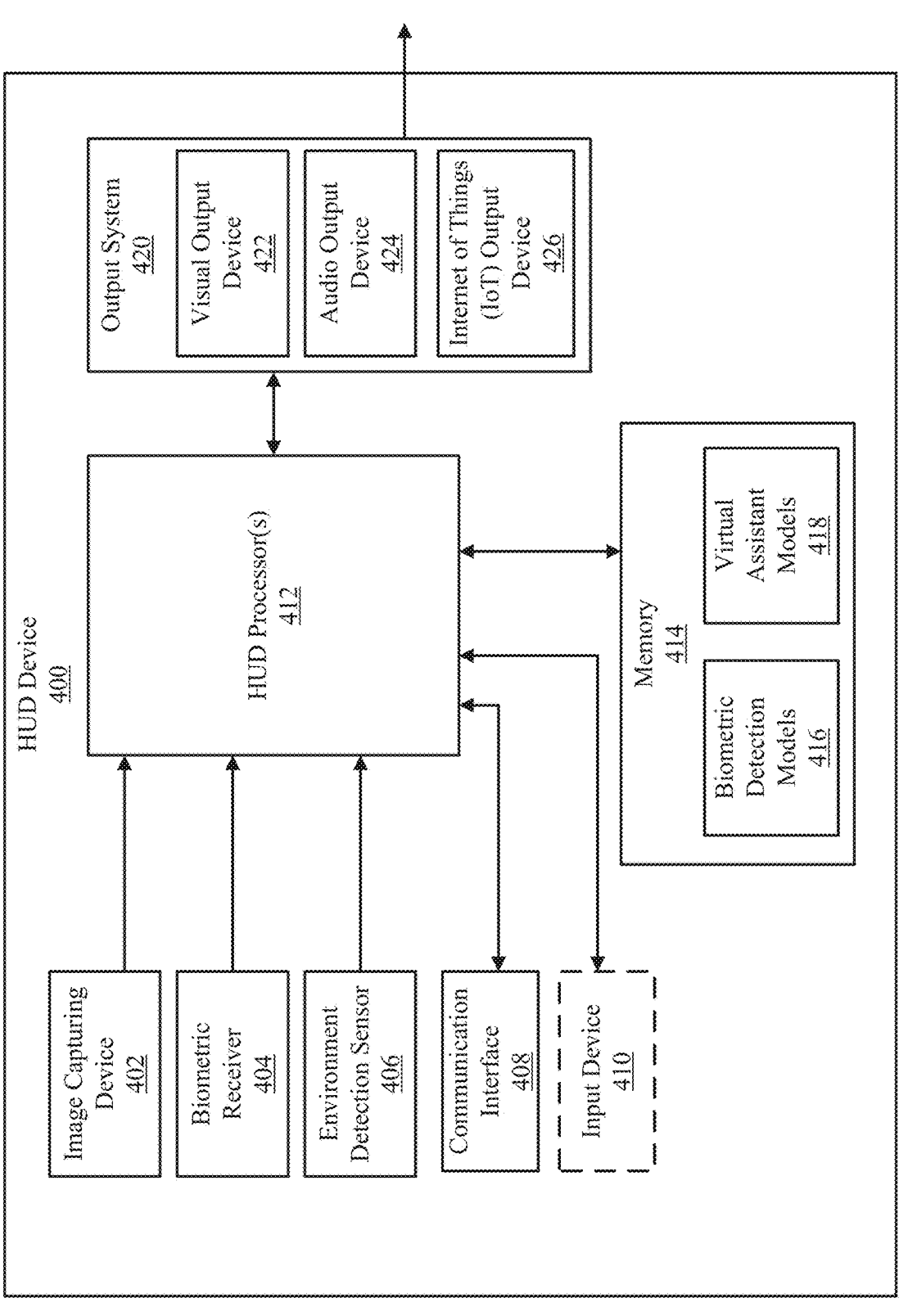
FIG. 4 is a simplified block diagram depicting an exemplary HUD device providing the virtual assistant in accordance with one or more examples of the present application.

Additionally, and/or alternatively, the HUD device may provide for the biometric detection models (e.g., rPPG model) and/or virtual assistant models. This is described in FIG. 4. For instance, FIG. 4 is a simplified block diagram depicting an exemplary HUD device providing the virtual assistant in accordance with one or more examples of the present application. For example, as shown in FIG. 4, a HUD device 400 (e.g., similar to user device 104 and/or HUD device 312) may include receivers and/or sensors (e.g., image capturing device 402, biometric receiver 404, environment detection sensor 406, and/or input device 410) for obtaining (e.g., sensing, receiving, collecting) user feedback, one or more processors 412 for inputting the obtained feedback to one or more biometric detection models 416 and/or virtual assistant models 418 in memory 414, and/or the one or more processors 412 for inputting the obtained feedback and/or an output of the one or more biometric detection models 416 and/or virtual assistant models 418 to an output system 420 for outputting a response to the user via one or more output devices (e.g., visual output device 422, audio output device 424, and/or an internet of things (IOT) output device 426). The HUD device 400 may obtain user feedback using any of the image capturing device 402, biometric receiver 404, environment detection sensor 406, and/or input device 410 alone or in combination, may input obtained the obtained feedback into the one or more biometric detection models 416 and/or virtual assistant models 418 alone or in combination, and may output a response to the user using one or more of the visual output device 422, audio output device 424, and/or an IoT output device 426 alone or in combination.

Additionally, and/or alternatively, the HUD device may provide for the virtual assistant models to assist a user's driving. For instance, the image capturing device 402 and/or the environment detection sensor 406 (e.g., a sound navigation and ranging (SONAR) sensor, light detection and ranging (LIDAR) sensor, temperature sensor) may obtain (e.g., detect) data on a vehicle's surroundings (e.g., road conditions, nearby drivers, visibility) and/or a vehicle's cabin (e.g., humidity, temperature) associated with potential hazards and/or distractions. The HUD device 400 may input this hazard data to the one or more virtual assistant models 418 to determine the presence of a hazard and/or distraction, and provide an alert to the driver (e.g., using the output system 420), in real-time, regarding the determined hazard and/or distraction.

For instance, the HUD device 400 may use the biometric receiver 404 to obtain biometric feedback (infrared scans, heart rate detection, blood pressure detection, temperature recordings) of the user upon request from the user, upon request from an enterprise computing system (e.g., enterprise computing system 301), or passively at regularly scheduled intervals (e.g., every 30 seconds, every hour, every minimum rate of acceleration, every time the vehicle in which the HUD device 400 is deployed is turned on). Additionally, and/or alternatively, the HUD device 400 may use one or more environment detection sensors 406 to obtain environmental feedback data (e.g., humidity of a vehicle cabin space, temperature of the vehicle cabin space) of the user's vehicle in which the HUD device 400 is deployed, and/or, optionally, use one or more input devices 410 (e.g., wearable devices such as first wearable device 512 and second wearable device 514 of FIG. 5) to obtain biometric feedback from the user. The HUD device 400 may use the one or more HUD processors 412 to input the user feedback (e.g., the obtained feedback from the biometric receiver 404, environment detection sensor 406, and/or input device 410) to the one or more biometric detection models 416 (e.g., an rPPG model similar to the one or more rPPG models 308, a heart rate model, a humidity model) to output a biometric condition of the user (e.g., fever, fatigue, heart arrhythmia). The HUD device 400 may use the one or more HUD processors 412 to input the output biometric condition of the user to the one or more virtual assistant models 418 to output a communication to the user. The HUD device 400 may use the one or more HUD processors 412 to provide (e.g., input) the communication to the output system 420. For instance, the HUD device 400 may use the visual output device 422 to project a request for user consent to act on the biometric condition (e.g., "it appears you may have the seasonal flu. May I set up a consultation with a medical professional near you?"). The HUD device 400 may obtain consent by using the image capturing device 402 to obtain an image of a gesture (e.g., thumbs up gesture, American sign language for "yes") performed by the user. For instance, the HUD device may refocus and/or reposition the image capturing device 402 to move from a user's face (e.g., after obtaining facial images and/or scans for the rPPG model) to a user's hand upon detecting motion in the region of a user's hand, and obtain one or more images of a user's hand performing the gesture.

Additionally, and/or alternatively, the HUD device 400 may include environment detection sensor 406 which includes humidity sensors. The humidity sensors may collect humidity/water vapor content information (e.g., moisture content) as biometric feedback. For example, the humidity sensor obtains moisture content within the area surrounding the HUD device 400. The HUD processor(s) 412 may input the biometric feedback to the one or more biometric detection models 416 to determine, based on the moisture content, whether the individual 102 has one or more health conditions. For instance, the biometric detection models 416 may compare the received moisture content to one or more thresholds to determine whether the individual 102 has one or more health conditions such as a cold sweat. For example, by inputting the biometric feedback (e.g., temperature information) into the biometric detection models 416, the biometric detection models 416 may determine whether the moisture content indicates there is an individual 102 within the vicinity of the HUD device 400 and whether the individual 102 has one or more health conditions.

The HUD device 400 may use the one or more HUD processors 412 to input the user's obtained feedback (e.g., the thumbs up gesture) to the one or more virtual assistant models 418 (e.g., one or more multi-modal language models) to determine whether further action will be taken. For instance, based on the user's provided consent (e.g., the thumbs up gesture), the one or more virtual assistant models 418 may output a request to the communication interface 408 to obtain service provider data from one or more service provider systems (e.g., one or more of service provider systems 314, 316, and/or 318 as in FIG. 3). The HUD device 400 may use the one or more HUD processors to provide (e.g., input) the request for service provider data associated with the output from the one or more virtual assistant models 418 to the communication interface 408, and provide the service provider data obtained by the communication 408 into the one or more virtual assistant models 418 to output a response to the user. The HUD device 400 may use the one or more HUD processors 412 to input the response to the user to one or more output devices of the output system 420. For instance, the HUD device 400 may use the one or more HUD processors 412 to input the response to the IoT output device 426 to output an appointment scheduling to a user's digital calendar of a smart home system and/or input the response to the audio output device 422 to produce an audio to the user confirming the scheduled date, time, and/or location of the appointment.

Additionally, and/or alternatively, the HUD device 400 may provide one or more functionalities for user convenience. For example, the HUD device 400 may provide a user interface using the output system 420 (e.g., visual output device 422). The user interface may display communications (e.g., responses, alerts, advertisements) to the user using one or more media (e.g., text, symbols, colors, images, videos). For instance, the user interface may display a communication in a windowed format with a colored window. By receiving user input from a communication interface 408 and/or an input device 410, the HUD device 400 may modify how a communication is provided. For example, the HUD device 400 may receive user input directing the HUD device 400 to provide alert communications with a red windowed frame and to provide response communications with a blue windowed frame. Additionally, and/or alternatively, the HUD device 400 may receive user input directing the HUD device 400 to provide, using the audio output device 424 and/or IoT output device 426, alert communications with a first sound and response communications with a second sound.

For a further example, the HUD device 400 may provide interactive navigation features, such as the ability to select points of interest directly from the HUD device or overlaying information about nearby attractions or amenities onto a navigation interface. For instance, the HUD device 400 may obtain information from the internet associated with locations displayed in a navigation window of the HUD device 400. The HUD device 400 may obtain the associated information using the one or more virtual assistant models and generate additional displays within the navigation window displaying the obtained information to the user.

Figure 5:
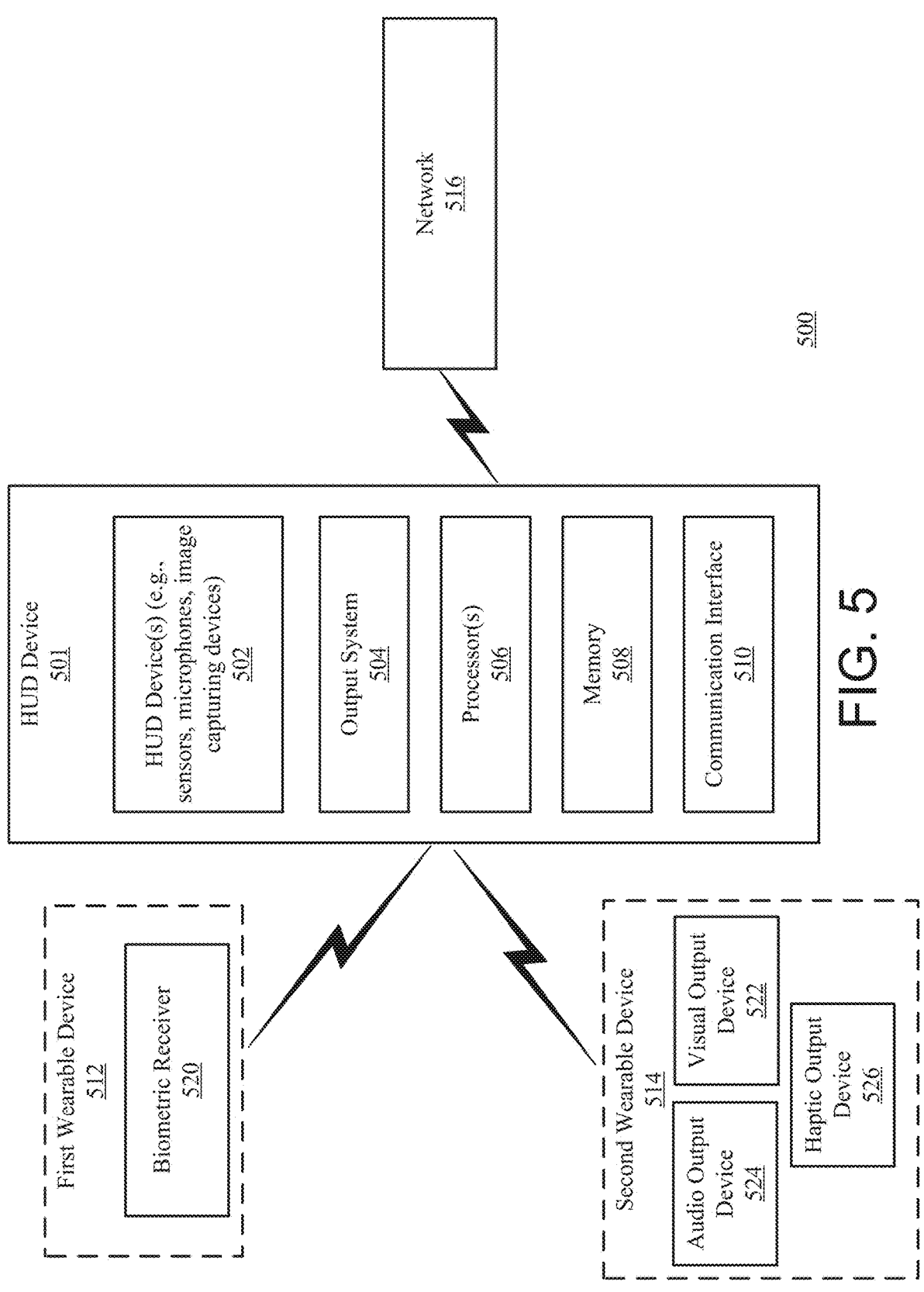
FIG. 5 is a simplified block diagram depicting an exemplary HUD device in communication with one or more wearable devices for collecting biometric and/or sensory data in accordance with one or more example of the present application.

Additionally, and/or alternatively, the HUD device may obtain user feedback and provide a response using one or more wearable devices. This is described in FIG. 5. For instance, FIG. 5 is a simplified block diagram of an environment depicting an exemplary HUD device in communication with one or more wearable devices for collecting biometric and/or sensory data in accordance with one or more example of the present application. For example, environment 500 may include the HUD device 501 (e.g., similar to HUD device 400), a first wearable device 512 (e.g., a heart rate monitor, thermometer, and/or blood pressure monitor similar to biometric receive 404) including a biometric receiver for obtaining biometric feedback from a user (e.g., a heart rate, body temperature, vehicle cabin temperature, blood pressure) and a second wearable device 514 including an audio output device 524, a visual output device 522, and/or a haptic output device 526. Additionally, and/or alternatively, the first wearable device 512 and the second wearable device 514 may be combined into a single device (e.g., a smart watch).

The HUD device 501 may obtain (e.g., receive) the biometric feedback and/or further biometric feedback data in addition to the biometric feedback data obtained by the HUD device from the first wearable device 512 using the communication interface 510 (e.g., similar to communication interface 408 and/or IoT output device 426) and/or one or more processors 506 (e.g., similar to one or more HUD processors 412). The HUD device 501 may obtain further biometric data (e.g., associated with and/or complimentary to the feedback data obtained by the biometric receiver 520) using the one or more HUD device(s) 502 such as one or more images of the user for determining heart rate, blood oxygen saturation, and respiration rate using one or more rPPG models (e.g., similar to the one or more rPPG models 308), one or more environmental conditions (e.g., humidity of the vehicle cabin similar to environment detection sensor 406), and one or more sounds using the microphone (e.g., a cough of the user). Additionally, and/or alternatively, the HUD device 501 may obtain the further biometric data based on obtaining the biometric feedback from the first wearable device 512 (e.g., the biometric feedback indicating a potential condition and HUD device 501 obtain further data to confirm or deny potential condition). Additionally, and/or alternatively, a user may request that the first wearable device 512 obtain biometric feedback and provide the biometric feedback to HUD device 501. Additionally, and/or alternatively, the HUD device 501 may direct the first wearable device 501 to obtain biometric feedback from the user (e.g., based on first obtaining biometric data using the one or HUD device(s) 502 indicating a potential condition). For example, the HUD device 501 may use one or more virtual assistant models to generate a function call to the first wearable device 512 to obtain biometric data using the biometric receiver 520 and generate a function call to a second wearable device 514 to use visual output device 522 to display a notification that first wearable device 512 is obtaining biometric data.

The HUD device 501 may then provide the biometric feedback and/or further data to one or more models in memory 508 (e.g., the one or more biometric detection models 416 and/or virtual assistant models 418) using the one or more processor(s) 506. The HUD device 501 may provide the biometric feedback data, the further biometric data, and/or an output of the one or more biometric detection models 416 and/or virtual assistant models 418 from memory 508 to the network 516 using the one or more processor(s) 506 and communication interface 510. The HUD device 501 may obtain a response from the network 516 (e.g., responsive data from a provider system as in environment 300). The HUD device 501 may then use the one or more processors 506 to provide data to the output system 504 for outputting an indication to the user using output system 504 and/or direct the second wearable device 514 to produce an output to the user using the audio output device 525, visual output device 522, and/or haptic output device 526. For example, the HUD device 501 may use output system 504 to produce a textual and/or image based response for the user and/or direct the second wearable device 514 to produce a vibration using the haptic output device 526, a sound using the audio output device 524, and/or display text using the visual output device 522 directing the user to view the response produced by the output system 504. Additionally, and/or alternatively, the HUD device 512 may direct the second wearable device 514 to produce the response for the user. For example, the second wearable device 514 may display the textual and/or image based response using the audio output device 524, read the response out loud for the user using audio output device 524, and/or translate the response into Morse code using the haptic output device 526.

Figure 6:
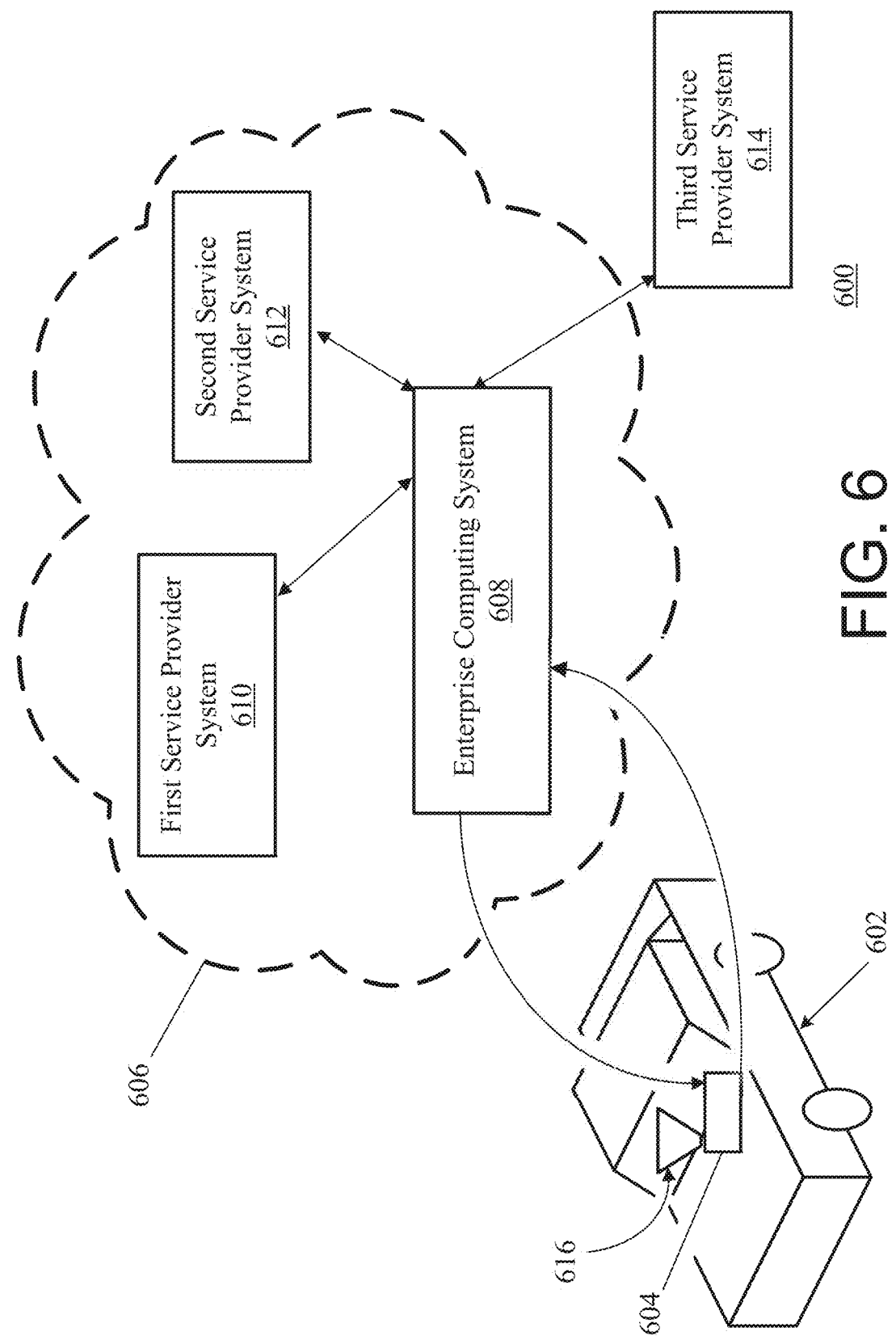
FIG. 6 is a simplified diagram depicting an exemplary HUD integrated virtual assistant environment in accordance with one or more examples of the present application.

The HUD device may be deployed in a vehicle of a user and communicate with cloud based systems. For example, as shown in the environment 600 of FIG. 6, a HUD device 604 may be deployed in a vehicle 602. The HUD device 604 may obtain biometric feedback of the user (e.g., similar to HUD devices 312, 400, and/or 501) in the vehicle 602. The HUD device 604 may provide this biometric feedback directly to an enterprise computing system 608 (e.g., similar to HUD device 312) located separately from the vehicle 602 (e.g., a cloud provisioned server). Additionally, and/or alternatively, the HUD device 604 may provide the output of one or more models and/or the biometric feedback to the separately located enterprise computing system 608. For example, the HUD device 604 may provide the biometric feedback of the user (elevated heart rate), a biometric condition of the user (high blood pressure) determined by one or more biometric detection models, and a query (e.g., a status of a blood pressure prescription) to the enterprise computing system 608.

The enterprise computing system 608 may communicate with one or more service provider systems within an enterprise network 606 (e.g., first service provider system 610 and/or second provider system 612) and/or one or more service provider systems not included in the enterprise network 606 (e.g., third service provider system 614). For example, the enterprise may provide the first service (e.g., pharmaceutical services) associated with the first service provider system 610 and the second service (e.g., medical examination) associated with the second service provider system 612, while the enterprise may not provide the third service (e.g., navigation, health insurance, user calendar management) associated with the third service provider system 614. The enterprise computing system 608 may communicate within the enterprise network 606 using an enterprise network 606 infrastructure to obtain data from the first service provider system 610 and the second provider system 612 (e.g., authorization and pick up date of the blood pressure prescription is ready) and/or may communicate outside the enterprise network 606 using a third party infrastructure and/or communication infrastructure associated with the enterprise computing system 608 to obtain data from the third service provider system 614 (e.g., when the health insurance has verified payment of the blood pressure prescription). The enterprise computing system 608 (e.g., using the one or more virtual assistant models) may notify the user that the third service provider system 614 is outside of the enterprise network 606 before the enterprise computing system 608 communicates with the third service provider system 614 and request consent to communicate with the third service provider system, for example to maintain user privacy.

The enterprise computing system 608 may provide a response to the HUD device 604. For example, the enterprise computing system 608 may provide (e.g., using one or more language ML-AI models) a response indicating that the blood pressure prescription is approved by the health care provider and paid for by the user's health insurance provider, and a time and location for collection of the blood pressure prescription. The HUD device 604 may produce a projection 616 (e.g., onto the windshield of vehicle 602 and/or a provided projection surface for the HUD device 604) displaying the status of the prescription and time and location for collection of the blood pressure prescription for the user to view and/or read. Additionally, and/or alternatively, the HUD device 604 may project a projection 616 onto a surface external to the HUD device 604 of an output (e.g., a response, an avatar) of the one or more virtual assistant models onto a windshield, mirror, sliding glass window, and/or passenger seat of the vehicle 602.

Figure 7:
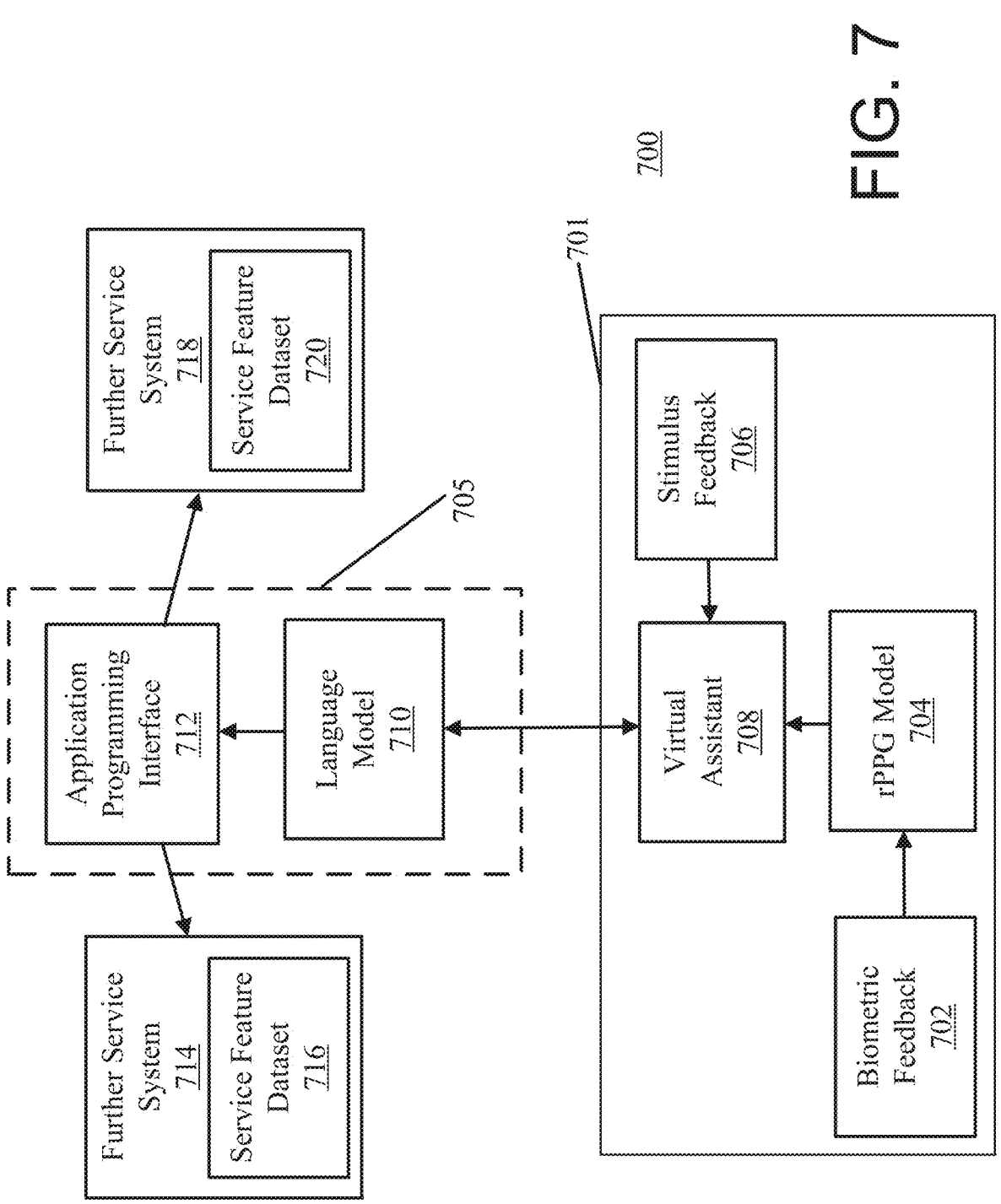
FIG. 7 is a depiction of an exemplary process for obtaining service provider data using a virtual assistant in accordance with one or more examples of the present application.

FIG. 7 depicts an exemplary environment 700 for a flow of data when obtaining service provider data using a virtual assistant. For example, FIG. 7 may include a HUD device 701 (e.g., similar to HUD device 312, 400, 501, and/or 604), an enterprise computing system 705 (e.g., similar to enterprise computing system 301 and/or 608), and further service systems 714 and/or 718. The HUD device 701 may obtain biometric feedback 702 from a user and provide the biometric feedback 702 to the rPPG model 704. The HUD device 701 may use the rPPG model 704 (e.g., similar to the one or more rPPG models of biometric detection models 416) to determine a biometric condition of the user based on the biometric feedback 702 and provide the biometric condition and/or the biometric feedback 702 to a virtual assistant 708 (e.g., one or more language models that provide assistance to a user). For example, the HUD device may obtain biometric feedback 702 based on one or more images of a user's face. The rPPG model may determine a biometric condition (e.g., elevated heart rate) based on changes to a skin color of the user's face and/or a base heart rate of the user and provide the biometric condition to the virtual assistant 708.

The HUD device 701 may provide the output of the rPPG model 704 (e.g., the biometric condition) directly to the virtual assistant 708. Additionally, and/or alternatively, the HUD device 701 may provide the output of the rPPG model 704 to a prompt engine to generate a prompt based on the rPPG model 704 output and/or a prompt template, and provide the prompt to a language model (e.g., SLM) of the virtual assistant 708. For instance, the prompt engine may access a set of prompt templates (e.g., stored in memory 414) each including an indicator for when to use the respective template (e.g., an association of a given biometric condition and/or user input to a respective template). The prompt engine may then generate a prompt based on a prompt template selected based on the biometric condition. Additionally, and/or alternatively, the HUD device 701 may collect stimulus feedback 706 and provide the stimulus feedback 706 to the virtual assistant 708. For instance, the virtual assistant 708 provide a prompt to the user based on the received biometric condition requesting user consent to act on the biometric condition. The user may provide a gesture or verbal confirmation as stimulus feedback 706 indicating consent for the virtual assistant 708 to act on the biometric condition. Based on the biometric feedback 702, biometric condition, and/or the stimulus feedback 706, the virtual assistant 708 may provide a request to the enterprise computing system 705 for one or more language models 710. Additionally, and/or alternatively, the HUD device 701 may use the virtual assistant 780 to provide the request directly to the language model 710 of the enterprise computing system 705 (e.g., with a direction to input, by the enterprise computing system, the biometric feedback data to the one or more language models). The request may request data (e.g., information) associated with further service systems (e.g., further service system 714 and/or 718) to answer the request.

The enterprise computing system 705 may include one or more language models 710 and an API 712. The enterprise computing system 705 may obtain (e.g., receive) the request from the virtual assistant 708 of the HUD device 701 and provide the request to the one or more language models 710. The enterprise computing system 705 may use the one or more language models 710 to determine which service system contains information response to the request. For example, the one or more language models 710 may determine that, based on the received request, either the service feature dataset 716 of the further service system 714 or service feature dataset 720 of the further service system 718 contains information responsive to the request and use the API 712 to obtain the relevant data (e.g., information) from the service feature dataset 716 or 720 of the determined further service system 714 or 718, respectively. Additionally, and/or alternatively, the one or more language models may determine that, based on the received request, both service feature datasets 716 and 720 contain responsive data and use the API 712 to obtain the relevant data from both service feature datasets 716 and 720 of the determined further service systems 714 and 718. To allow the one or more language models 710 to obtain the relevant data from the further service systems 714 and/or 718, the API 712 provides the set of rules or protocols that enables the one or more language models 710 to communicate with the further service systems 714 and/or 718, even when the further service systems may not be included in the same enterprise network (e.g., enterprise network 606) of enterprise computing system 705. Additionally, and/or alternatively, each further service system 714 and/or 718 may have their own gateway for communication with the API 712 of the enterprise computing system 705.

For example, the HUD device 701 may obtain input from a user requesting availability for a medical provider covered by the user's health insurance (e.g., the user may ask a question to the HUD device 701) and the HUD device 701 may provide the input to the one or more language models 710. The one or more language models 710 may determine that the further service 714 is the user's health insurance system and contains service feature dataset 716 including data associated with the medical provider's covered by the user's health insurance policy. The one or more language models 710 may use the API 712 to obtain the data associated with covered medical providers from the service feature dataset 716 and determine, based on the obtained medical provider data, that further service system 718 is associated with one or more covered medical providers and contains service feature dataset 720 including data associated with the availability of the covered medical providers. For instance, the one or more language models 710 may provide a text format output to the API 712, and/or outputs formatted according to one or more communication protocols, structured protocols, or unstructured outputs. The one or more language models 710 may use the API 712 to obtain the data associated with the availability of the covered medical providers. Additionally, and/or alternatively, the language model 710 may determine, based on the request, that both further service system 714 and 718 contain data response to the request, and use the API 712 to obtain responsive data from both further service systems 714 and 718 simultaneously. The enterprise computing system 705 (e.g., based on an output of the one or more language models 710) may provide the data associated with covered medical providers and the data associated with the availability of the covered medical providers directly to the virtual assistant 708, and the virtual assistant 708 may determine a response for the user, such as "Medical provider A is available next week in the morning, 10 AM. Should I schedule this appointment?" or "Medical provider A is available next week in the morning, 10 AM and the afternoon, 2 PM. Should I schedule an appointment, and if so, at which time?" Additionally, and/or alternatively, the enterprise computing system 705 may provide the data associated with covered medical providers and the data associated with the availability of the covered medical providers to the one or more language models 710 to generate a response to the user, and the enterprise computing system 705 may provide this output response to the virtual assistant 708. Additionally, and/or alternatively, the virtual assistant 708 may obtain data from the service feature dataset 716 and/or 720 before providing a response to the user.

The enterprise computing system 705 may provide the obtained service system data to the one or more language models 710 to generate a response to the request, and provide the response to the virtual assistant 708. Additionally, and/or alternatively, the enterprise computing system 705 (e.g., using the one or more language models 710) may provide the obtained service system data directly to the virtual assistant 708, and the HUD device 701 may use the virtual assistant 708 to generate a response. For instance, based on the HUD device 701 obtaining biometric feedback 702, providing the biometric feedback 702, and using the rPPG model 704 to generate an indication that the user has a biometric condition (e.g., fever), the HUD device 701 may provide the biometric condition output from the rPPG model to the virtual assistant 708. The HUD device 701 may provide, to the language model 710 of the enterprise computing system 705, an output of the virtual assistant 708 requesting data from further service system 714 on the user's prescriptions. The language model 710 may obtain the output and use the API 712 to obtain prescription data from the service system 714 (e.g., provide a function call to the API 712 to obtain the prescription data from service feature data 716). The language model 710 may receive the prescription data from the API 712 and the enterprise computing system 705 may provide the prescription data and/or further text based information (e.g., reformatted data, timestamps indicating when the data was obtained, contextual data based on a user data set accessible by the language model 710) from the language model 710 to the virtual assistant 708. Based on the received prescription data and the biometric condition, the virtual assistant 708 may direct the HUD device 701 to generate a notification to the user (e.g., send a function call to a display device or audio output device of the HUD device 701 or associated wearable device) such as "have you taken your flu prescription today? If not, that may be the cause. If you have, should I schedule an appointment for you?"

FIG. 8 is an exemplary process 800 for providing a response to an indication of a user via a display device in accordance with one or more examples of the present application. The process 800 may be performed by a HUD device and/or enterprise computing system such as the HUD device 104 of FIG. 1 and the enterprise computing system 110 of FIG. 1. (e.g., HUD device 604, 701 and/or enterprise computing system 608, 705). Additionally, and/or alternatively, the HUD device and enterprise computing system may be the HUD device 312 and the enterprise computing system 301 of FIG. 3. Additionally, and/or alternatively, the HUD device and the enterprise computing system may be the HUD device 400 and/or 501 and the network 516. Additionally, and/or alternatively, the HUD device and enterprise computing system may be the HUD device 604 and the enterprise computing system 608 of FIG. 6. Additionally, and/or alternatively, the HUD device and enterprise computing system may be the HUD device 701 and the enterprise computing system 705 of FIG. 7. Furthermore, it will be understood that any of the following blocks may be performed in any suitable order. The descriptions, illustrations, and processes of FIG. 8 are merely exemplary of the enterprise computing system and the process 800 may use other descriptions, illustrations, and processes (e.g., a HUD device) to provide a response to an indication of a user.

At block 802, the enterprise computing system receives, from a display device, an indication based on sensory information obtained from a user using the display device. For example, at block 802, a display device (e.g., a HUD device 400) has obtained biometric, audio, and/or visual data of a user (e.g., using one or more of an image capturing device 402, a biometric receiver 404 and/or 520, and/or an environment detection sensor 406), and generated an indication (e.g., images of a user, a biometric condition of the user determined by one or more rPPG models 308 and/or biometric detection models 416, and/or confirmation of consent from the user), which the enterprise computing system (e.g., enterprise computing system 301) receives from the display device. Additionally, and/or alternatively, the display device (e.g., HUD 604) may be located in a vehicle (e.g., vehicle 602), and enterprise computing system may be separately located (e.g., cloud-provisioned and/or separately located server for enterprise computing system 608) and receive the indication via one or more forms of wireless transmission. For example the display device may provide, as the indication, a biometric condition of the user to the enterprise computing system determined by inputting the obtained biometric feedback (e.g., obtained as sensory information) to one or more biometric condition models. In this case, the biometric condition would indicate a condition that the enterprise computing system may and/or should respond to (e.g., reminding the user to seek treatment, collect medication, and/or adjust driving behavior). Additionally, and/or alternatively, the enterprise computing system may receive, from the display device, sensory information including a gesture or auditory response representative of confirmation of the user's consent for the enterprise computing system to seek responsive information from a service provider system, which the user may provide to the display device by giving a gesture (e.g., thumbs up) and/or verbally providing consent (e.g., speaking "yes, go ahead").

The enterprise computing system may generate a prompt (e.g., for input to an ML-AI model) based on the biometric condition data of the user, where the prompt includes a request for service provider data associated with the biometric condition. For example, the enterprise computing system may input the biometric condition data of the user to a prompt engine to generate the prompt. Generating the prompt may be based on selecting, by the prompt engine, a first prompt template of a plurality of prompt templates of the prompt engine. For example, the prompt engine may have access to a memory file including a plurality of prompt templates that are each stored in memory with an association (e.g., an indicator) to a given request from the user or a biometric condition of the user that helps the prompt engine select a relevant prompt template, such that the first prompt template is stored with an association to the determined biometric condition data. The prompt engine may then produce a prompt based on completing the prompt template with data provided by the enterprise computing system.

At block 804, the enterprise computing system inputs a prompt associated with the indication to one or ML-AI language models to determine a service provider system of a plurality of service provider systems associated with the prompt. For example, at block 804, the enterprise computing system inputs a prompt related to the indication (e.g., a request for responsive information as in environment 700) to one or more language models (e.g., virtual assistant language models 310, language model 710) to determine that a service provider system (e.g., further service system 714 and/or 718) contains responsive information (e.g. which service provider system includes a service features dataset 716 and/or 720 containing information associated with and/or or responsive to the prompt).

The prompt may be based on the received indication. For instance, the enterprise computing system may provide, to the display device, a confirmation request based on determining an actionable status. The confirmation request may request the consent from the user associated with inputting the prompt to the one or more ML-AI language models For example, the confirmation request may request that the user provide consent to allow one or more virtual assistant models to provide an input to one or more further language models, wherein the input is associated with the sensory information, biometric condition, and/or a prompt based on the sensory information and/or the biometric condition. The display device may obtain the consent from the user (e.g., as part of the sensory information) and generate the indication based on obtaining the consent from the user. The enterprise computing system may then input the prompt to the one or more ML-AI language models based on obtaining the consent from the user. Additionally, and/or alternatively, the enterprise computing system may receive the biometric feedback data from the display device and generate the indication based on the biometric feedback data and the consent from the user associated with inputting the prompt to the one or more ML-AI language models. The prompt may then be associated with the biometric condition data of the user, and generated based on the biometric condition data of the user.

At block 806, the enterprise computing system obtains, from a common interface, service provider data associated with the prompt, wherein the common interface is commonly associated with each of the plurality of service provider systems. For instance, at block 806, the enterprise computing system obtains, from an API (e.g., using API 712), the service provider data (e.g., from service feature dataset 716) of the service provider (e.g., further service system 714) determined to be associated with the prompt received at block 804. For example, the enterprise computing system may access, by the common interface (e.g., API 712), a first service feature dataset (e.g., service feature dataset 716) of a first service provider system (e.g., further service system 714) of the plurality of service provider systems and obtain, from the first service feature dataset and by the common interface, first service provider data associated with the prompt. In this case, the enterprise computing system may input the first service provider data to the one or more ML-AI language models at block 808. The common interface (e.g., the API) may be commonly associated with of the service provider systems (e.g., further service systems 714 and/or 718) by being able to communicate with each of the service provider systems. For instance, the API may provide the set of rules and protocols through which each of the plurality of service provider systems may communicate with the API.

Additionally, and/or alternatively, the enterprise computing system may use the common interface (e.g., API 712) to provide the first service provider data (e.g., data obtained from service feature data 716 of service system 714) to a second service provider system (e.g., service system 718) of the plurality of service provider systems. The enterprise computing system may use the common interface to access a second service feature dataset (e.g., service feature dataset 720) of the second service provider system (e.g., further service system 718). For example, the enterprise computing system may provide data obtained from the first service system to the second service system, and obtain the data from the second service system based on the data provided to the second service system. The enterprise computing system may then obtain, from the second service feature dataset and by the common interface, second service provider data associated with the prompt and the first service provider data. For instance, the enterprise computing system may receive a prompt requesting available healthcare providers this week, obtain the healthcare providers covered by the user's insurance policy from the first service feature dataset, and provide the covered healthcare providers to the second service system to determine which of the covered healthcare providers have availability. Inputting the service provider data to the one or more ML-AI language models may then include inputting the first service provider and the second service provider data to the one or more ML-AI language models to generate a response to the prompt.

Additionally, and/or alternatively, the enterprise computing system may provide, to the display device, a further request to the user based on the obtained service provider data requesting a consent of the user to provide the first service provider data to the second service provider system. For instance, before providing data from the first service provider system to the second service provider system (e.g., before or after obtaining the data from the first service provider system), the enterprise computing system may request the user's consent to provide the data to the second service system (e.g., allowing the user to retain privacy or control over the data). The enterprise computing system may receive, from the display device, the consent of the user to provide the first service provider data to the second service provider system, for example through a user's gesture and/or spoken consent obtained as sensory information and an indication of confirmation of consent based on the user's gesture and/or spoken consent. The enterprise computing system may provide, by the common interface, the first service provider data to the second service provider system based on receiving the consent of the user to provide the first service provider data to the second service provider system.

At block 808, the enterprise computing system inputs the service provider data to the one or more ML-AI language models to generate a response to the prompt. For example, the enterprise computing system may provide the obtained service provider data to one or more virtual assistant language models (e.g., virtual assistant language models 310, language model 710) to generate a response based on (e.g., relying on, including) the obtained service provider data.

At block 810, the enterprise computing system provides the response to the user via the display device. For instance, the enterprise computing system may provide a control signal (e.g., direction, instruction) to the display device (e.g., HUD) for the display device to display (e.g., project onto the windshield, provide on a screen) the response to the user and/or notify the user of the response (e.g., vibrate a wearable device or produce a sound notifying the user the response is displayed).

A number of implementations have been described. Nevertheless, it will be understood that additional modifications may be made without departing from the scope of the inventive concepts described herein, and, accordingly, other examples are within the scope of the following claims. For example, it will be appreciated that the examples of the application described herein are merely exemplary. Variations of these examples may become apparent to those of ordinary skill in the art upon reading the foregoing description. The inventor expects skilled artisans to employ such variations as appropriate, and the inventor intends for the application to be practiced otherwise than as specifically described herein. Accordingly, this application includes all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

It will further be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein as being performed by computing devices and/or components thereof may be carried out by according to processor-executable instructions and/or installed applications corresponding to software, firmware, and/or computer hardware.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the application and does not pose a limitation on the scope of the application unless otherwise claimed. No language in the specification should be construed as indicating any non-claimed element as essential to the practice of the application.

The invention claimed is:

1. A system, comprising:

a heads up display (HUD) device for a vehicle, the HUD device comprising one or more biometric sensors, one or more assistant machine learning-artificial intelligence (ML-AI) language models, and one or more sensory output devices, the HUD device configured to:

obtain biometric feedback data of a user using the one or more biometric sensors;

input the biometric feedback data to one or more remote photoplethysmography (rPPG) models to determine biometric condition data of the user;

input, to the one or more assistant ML-AI language models, the biometric condition data to determine that the biometric condition data is actionable;

provide, to the user and from the one or more assistant ML-AI language models, a confirmation request for the user based on determining the biometric condition data is actionable, wherein the confirmation request requests a consent from the user to provide the biometric condition data from the vehicle to a cloud provisioned computing system;

obtain, from the user, the consent and provide the consent to the one or more assistant ML-AI language models;

provide, by the one or more assistant ML-AI language models, the biometric condition data and the consent from the vehicle to a cloud provisioned computing system; and generate an output for the user, using the one or more sensory output devices, based on a control signal received from the cloud provisioned computing system;

the cloud provisioned computing system, the cloud provisioned computing system configured to:

input a prompt associated with the received biometric condition data to one or more ML-AI language models, based on receiving the consent from the HUD device, to determine one or more service provider systems associated with the received biometric condition data and provide to a common interface a request for service provider data from the one or more service provider systems;

receive, from the one or more service provider system, the service provider data associated with the request; and provide the control signal to the HUD based on the service provider data; and one or more service provider devices comprising the one or more service provider systems, the one or more service provider devices configured to:

receive, from the cloud provisioned computing system, the request;

determine, based on the request and using a service provider dataset associated with the service provider system, the service provider data associated with the request; and provide, to the cloud provisioned computing system, the service provider data.

2. The system of claim 1, wherein the one or more biometric sensors comprise an imaging device, wherein the biometric feedback data comprises one or more images of the user obtained using the imaging device, and wherein inputting the biometric feedback data to the one or more rPPG models further comprises inputting the one or more images of the user to the one or more rPPG models to determine the biometric condition data of the user based on a physiological trait of the user.

3. The system of claim 1, wherein obtaining, from the user, the consent further comprises:

obtaining, from the user, a gesture performed by the user, wherein the gesture represents the consent of the user.

4. The system of claim 3, wherein the one or more assistant ML-AI language models are trained based on gesture training data, wherein the gesture training data comprises a plurality of gestures for a user to perform associated with a meaning of each gesture of the plurality of gestures.

5. The system of claim 1, wherein generating the output for the user using the one or more sensory output devices further comprises projecting the output onto a surface external to the HUD device.

6. The system of claim 1, wherein the HUD device is further configured to:

provide, to a vehicle device, a second control signal to generate a second output associated with the output generated by the HUD device.

7. The system of claim 1, wherein the HUD device is further configured to:

obtain, from a wearable device, further biometric feedback data associated with the biometric feedback data, and wherein inputting the biometric feedback data to the one or more rPPG models further comprises:

inputting the biometric feedback data and the further biometric feedback data to the one or more rPPG models to determine the biometric condition data of the user.

8. The system of claim 1, wherein the HUD device is further configured to obtain a plurality of instances of biometric feedback data, wherein each instance of biometric feedback data is obtained at a scheduled time interval, and wherein the biometric feedback data is obtained at one of the scheduled time intervals.

9. The system of claim 1, wherein the cloud provisioned computing system comprises the one or more rPPG models, wherein inputting the biometric feedback data to the one or more rPPG models further comprises:

providing, to the cloud provisioned computing system, the biometric feedback data and a direction to input, by the cloud provisioned computing system, the biometric feedback data to the one or more rPPG models, and wherein the HUD is further configured to:

receive, from the cloud provisioned computing system, the biometric condition data of the user.

10. A method comprising:

providing, to a display device, a confirmation request based on determining an actionable status, wherein the confirmation request requests a consent from a user associated with inputting a prompt to one or more machine learning-artificial intelligence (ML-AI) language models;

receiving, from the display device, an indication based on sensory information obtained from the user using the display device, comprising:

obtaining, by the display device, the consent from the user; and generating, by the display device, the indication based on the obtained consent from the user;

inputting the prompt associated with the indication to the one or more ML-AI language models, based on obtaining the consent of the user, to determine a service provider system of a plurality of service provider systems associated with the prompt, wherein the prompt is based on the indication;

obtaining, from a common interface, service provider data associated with the prompt, wherein the common interface is commonly associated with each of the plurality of service provider systems;

inputting the service provider data to the one or more ML-AI language models to generate a response to the prompt; and providing the response to the user via the display device.

11. The method of claim 10, wherein the sensory information comprises the consent from the user associated with inputting the prompt to the one or more ML-AI language models.

12. The method of claim 10, wherein the sensory information comprises biometric feedback data, and wherein the method further comprises:

inputting the indication to one or more ML-AI biometric detection models to determine biometric condition data of the user; and generating the prompt based on the biometric condition data of the user, wherein the prompt comprises a request for the service provider data associated with the biometric condition.

13. The method of claim 12, wherein generating the prompt further comprises:

inputting the biometric condition data of the user to a prompt engine to generate the prompt based on selecting, by the prompt engine, a first prompt template of a plurality of prompt templates of the prompt engine, wherein the first prompt template is stored with an association to the determined biometric condition data.

14. The method of claim 10, wherein the sensory information comprises biometric feedback data and the consent from the user, wherein the indication is generated based on the biometric feedback data and the consent from the user associated with inputting the prompt to the one or more ML-AI language models, wherein the prompt is associated with the biometric condition data of the user, wherein receiving, from the display device, the indication further comprises receiving, from the display device, the biometric feedback data, wherein the method further comprises:

inputting the biometric feedback data to one or more ML-AI biometric detection models to determine biometric condition data of the user;

providing, to the display device the confirmation request based on determining the biometric condition data is actionable, wherein the confirmation request requests the consent from the user associated with inputting the prompt to the one or more ML-AI language models; and generating the prompt based on the biometric condition data of the user.

15. The method of claim 10, wherein obtaining, from the common interface, the service provider data further comprises:

accessing, by the common interface, a first service feature dataset of a first service provider system of the plurality of service provider systems; and obtaining, from the first service feature dataset and by the common interface, first service provider data associated with the prompt, wherein inputting the service provider data to the one or more ML-AI language models further comprises inputting the first service provider data to the one or more ML-AI language models.

16. The method of claim 15, wherein obtaining, from the common interface, the service provider data further comprises:

providing, by the common interface, the first service provider data to a second service provider system of the plurality of service provider systems;

accessing, by the common interface, a second service feature dataset of the second service provider system; and obtaining, from the second service feature dataset and by the common interface, second service provider data associated with the prompt and the first service provider data, wherein inputting the service provider data to the one or more ML-AI language models further comprises inputting the first service provider and the second service provider data to the one or more ML-AI language models.

17. The method according to claim 16, wherein the method further comprises:

providing, to the display device, a further request to the user based on the obtained service provider data requesting a consent of the user to provide the first service provider data to the second service provider system; and receiving, from the display device, the consent of the user to provide the first service provider data to the second service provider system, and wherein providing, by the common interface, the first service provider data to the second service provider system is based on receiving the consent of the user to provide the first service provider data to the second service provider system.

18. A non-transitory computer-readable medium having processor-executable instructions stored thereon, wherein the processor-executable instructions, when executed, facilitate:

providing, to a display device, a confirmation request based on determining an actionable status, wherein the confirmation request requests a consent from a user associated with inputting a prompt to one or more machine learning-artificial intelligence (ML-AI) language models;

receiving, from the display device, an indication based on sensory information obtained from the user using the display device, comprising:

obtaining, by the display device, the consent from the user; and generating, by the display device, the indication based on the obtained consent from the user;

inputting the prompt associated with the indication to the one or more ML-AI language models, based on obtaining the consent of the user, to determine a service provider system of a plurality of service provider systems associated with the prompt, wherein the prompt is based on the indication;

obtaining, from a common interface, service provider data associated with the prompt, wherein the common interface is commonly associated with each of the plurality of service provider systems;

inputting the service provider data to the one or more ML-AI language models to generate a response to the prompt; and providing the response to the user via the display device.

19. The non-transitory computer-readable medium of claim 18, wherein the sensory information comprises biometric feedback data, and wherein the processor-executable instructions, when executed, further facilitate:

inputting the indication to one or more ML-AI biometric detection models to determine biometric condition data of the user; and generating the prompt based on the biometric condition data of the user, wherein the prompt comprises a request for the service provider data associated with the biometric condition.

20. The non-transitory computer-readable medium of claim 19, wherein generating the prompt further comprises:

inputting the biometric condition data of the user to a prompt engine to generate the prompt based on selecting, by the prompt engine, a first prompt template of a plurality of prompt templates of the prompt engine, wherein the first prompt template is stored with an association to the determined biometric condition data.

* * * * *